(12) United States Patent
Mazanec

(10) Patent No.: US 11,471,689 B2
(45) Date of Patent: Oct. 18, 2022

(54) COCHLEAR IMPLANT STIMULATION CALIBRATION

(71) Applicant: Envoy Medical Corporation, White Bear Lake, MN (US)

(72) Inventor: Paul R. Mazanec, Ham Lake, MN (US)

(73) Assignee: Envoy Medical Corporation, White Bear Lake, MN (US)

( * ) Notice: Subject to any disclaimer, the term of this patent is extended or adjusted under 35 U.S.C. 154(b) by 133 days.

(21) Appl. No.: 17/109,305

(22) Filed: Dec. 2, 2020

(65) Prior Publication Data

US 2022/0168581 A1 Jun. 2, 2022

(51) Int. Cl.
*A61N 1/37* (2006.01)
*A61N 1/372* (2006.01)
(Continued)

(52) U.S. Cl.
CPC ....... *A61N 1/37241* (2013.01); *A61N 1/0541* (2013.01); *A61N 1/36038* (2017.08);
(Continued)

(58) Field of Classification Search
CPC .......... A61N 1/36036–36039; A61N 1/36157; A61N 1/37241
See application file for complete search history.

(56) References Cited

U.S. PATENT DOCUMENTS 2,827,041 A * 3/1958 Pierson ..................... A61N 1/32
607/76
4,400,590 A 8/1983 Michelson
(Continued)

FOREIGN PATENT DOCUMENTS

CN 104394930 A 3/2015
CN 110086237 A 8/2019
(Continued)

OTHER PUBLICATIONS

PCT International Search Report and Written Opinion dated Mar. 14, 2022 for related International Application No. PCT/US2021/060714, 10 pages.

(Continued)

*Primary Examiner* — Eric D. Bertram
(74) *Attorney, Agent, or Firm* — Fredrikson & Byron, P.A.

(57) ABSTRACT

Cochlear implant systems can include a cochlear electrode and a stimulator in electrical communication with the cochlear electrode. The stimulator can be in communication with a controller, which is in communication with a testing circuit and a switching network. The stimulator can include a plurality of source elements. The controller can control the switching network to place the plurality of source elements into communication with the testing circuit. The controller can further cause one of the plurality of source elements to emit an electrical current and can determine an amount of electrical current emitted from the source element using the testing circuit. The controller can compare the determined amount of electrical current emitted by the source element with a prescribed current. The controller can adjust the output of each of the plurality of source elements based on the determined amount of electrical current emitted by the stimulator.

28 Claims, 11 Drawing Sheets

(51) Int. Cl.
*A61N 1/36* (2006.01)
*A61N 1/05* (2006.01)
*A61N 1/378* (2006.01)
*G01R 31/28* (2006.01)

(52) U.S. Cl.
CPC ......... *A61N 1/36157* (2013.01); *A61N 1/378* (2013.01); *A61N 1/37223* (2013.01); *G01R 31/282* (2013.01)

(56) References Cited

U.S. PATENT DOCUMENTS

| | | |
|---|---|---|
| 4,495,384 A | 1/1985 | Scott et al. |
| 4,729,366 A | 3/1988 | Schaefer |
| 4,850,962 A | 7/1989 | Schaefer |
| 4,918,745 A | 4/1990 | Hutchison |
| 5,540,095 A | 7/1996 | Sherman et al. |
| 5,762,583 A | 6/1998 | Adams et al. |
| 6,195,585 B1 | 2/2001 | Karunasiri et al. |
| 6,212,431 B1 | 4/2001 | Hahn et al. |
| 6,259,951 B1 | 7/2001 | Kuzma et al. |
| 6,272,382 B1 | 8/2001 | Faltys et al. |
| 6,308,101 B1 | 10/2001 | Faltys et al. |
| 6,358,281 B1 | 3/2002 | Berrang et al. |
| 7,225,028 B2 | 5/2007 | Della Santina et al. |
| 7,319,906 B2 | 1/2008 | Kuzma et al. |
| 7,524,278 B2 | 4/2009 | Madsen et al. |
| 8,554,329 B1 | 10/2013 | Mann et al. |
| 8,655,449 B2 | 2/2014 | Haller et al. |
| 9,716,952 B2 | 7/2017 | Mauger |
| 2002/0039425 A1 | 4/2002 | Burnett et al. |
| 2002/0099421 A1 | 7/2002 | Goldsmith et al. |
| 2005/0033384 A1 | 2/2005 | Sacha |
| 2005/0197677 A1 | 9/2005 | Stevenson |
| 2006/0122664 A1 | 6/2006 | Sacha et al. |
| 2006/0183965 A1 | 8/2006 | Kasic, II et al. |
| 2008/0195179 A1 | 8/2008 | Quick |
| 2008/0300658 A1 | 12/2008 | Meskens |
| 2009/0018616 A1 | 1/2009 | Quick et al. |
| 2009/0082831 A1* | 3/2009 | Paul ............... A61N 1/36031 607/59 |
| 2009/0187233 A1 | 7/2009 | Stracener |
| 2009/0192565 A1 | 7/2009 | Lee et al. |
| 2010/0030012 A1 | 2/2010 | Meskens |
| 2010/0042183 A1 | 2/2010 | Beck |
| 2010/0317913 A1 | 12/2010 | Conn et al. |
| 2011/0082521 A1 | 4/2011 | Botros et al. |
| 2011/0116669 A1 | 5/2011 | Karunasiri |
| 2011/0137180 A1 | 6/2011 | Johnson et al. |
| 2011/0144719 A1 | 6/2011 | Perkins et al. |
| 2011/0160808 A1* | 6/2011 | Lyden ................ A61N 1/37 607/63 |
| 2011/0280426 A1 | 11/2011 | Bachler |
| 2011/0295331 A1 | 12/2011 | Wells et al. |
| 2012/0215285 A1 | 8/2012 | Tahmasian et al. |
| 2012/0277835 A1* | 11/2012 | Della Santina ...... A61N 1/3605 607/137 |
| 2013/0018216 A1 | 1/2013 | Beckerle et al. |
| 2013/0023953 A1 | 1/2013 | van den Honert |
| 2013/0193914 A1 | 8/2013 | Gaddam et al. |
| 2013/0223664 A1 | 8/2013 | Meskens et al. |
| 2013/0238048 A1* | 9/2013 | Almendinger .......... H02J 7/007 607/40 |
| 2013/0238055 A1 | 9/2013 | Marnfeldt et al. |
| 2013/0268025 A1 | 10/2013 | Ranu |
| 2013/0278226 A1 | 10/2013 | Cong et al. |
| 2013/0317584 A1 | 11/2013 | Stevenson et al. |
| 2014/0058482 A1 | 2/2014 | Gupta et al. |
| 2014/0247954 A1 | 9/2014 | Hall et al. |
| 2014/0270211 A1 | 9/2014 | Solum et al. |
| 2014/0275730 A1 | 9/2014 | Lievens et al. |
| 2014/0309712 A1 | 10/2014 | Masaki et al. |
| 2014/0350652 A1 | 11/2014 | Suwito |
| 2015/0125012 A1 | 5/2015 | Sabin |
| 2015/0174416 A1 | 6/2015 | Angara et al. |
| 2015/0224312 A1 | 8/2015 | Platz et al. |
| 2015/0256945 A1 | 9/2015 | Mazanec |
| 2015/0374988 A1 | 12/2015 | Laudanski |
| 2015/0375003 A1 | 12/2015 | Meskens |
| 2016/0227333 A1 | 8/2016 | Babico |
| 2017/0043162 A1 | 2/2017 | Lopez-Poveda |
| 2017/0077938 A1 | 3/2017 | Heubi |
| 2017/0094396 A1 | 3/2017 | Chandramohan et al. |
| 2017/0161449 A1 | 6/2017 | Meskens |
| 2017/0259072 A1 | 9/2017 | Newham et al. |
| 2017/0360364 A1 | 12/2017 | Heasman et al. |
| 2018/0028811 A1 | 2/2018 | Van Gerwen et al. |
| 2018/0028827 A1 | 2/2018 | Schilling et al. |
| 2018/0041848 A1 | 2/2018 | Nielsen et al. |
| 2018/0050197 A1 | 2/2018 | Mazanec et al. |
| 2018/0050198 A1 | 2/2018 | Mazanec et al. |
| 2018/0050203 A1 | 2/2018 | Mazanec et al. |
| 2018/0059870 A1 | 3/2018 | Krah |
| 2018/0264269 A1 | 9/2018 | Meadows |
| 2018/0333577 A1 | 11/2018 | Nygard et al. |
| 2019/0045308 A1 | 2/2019 | Chen et al. |
| 2019/0046116 A1 | 2/2019 | Shah et al. |
| 2020/0238075 A1 | 7/2020 | Mazanec et al. |
| 2020/0269034 A1 | 8/2020 | Mazanec et al. |
| 2020/0269035 A1 | 8/2020 | Mazanec et al. |
| 2020/0269047 A1 | 8/2020 | Mazanec et al. |
| 2020/0269048 A1 | 8/2020 | Mazanec et al. |
| 2020/0269057 A1 | 8/2020 | Mazanec et al. |
| 2020/0269058 A1 | 8/2020 | Mazanec et al. |
| 2021/0135704 A1 | 5/2021 | El-Hoiydi et al. |
| 2021/0187293 A1 | 6/2021 | Friedling |
| 2021/0361194 A1* | 11/2021 | Arab ................ A61N 1/36031 |

FOREIGN PATENT DOCUMENTS

| | | |
|---|---|---|
| DE | 4419070 A1 | 12/1994 |
| DE | 60107062 T2 | 11/2005 |
| DE | 102013214049 B4 | 3/2015 |
| EP | 1043914 A2 | 10/2000 |
| EP | 1683544 B1 | 11/2010 |
| EP | 2884766 B1 | 2/2018 |
| TW | 201142830 A | 12/2011 |
| WO | 2007137032 A2 | 11/2007 |
| WO | 2010056768 A1 | 5/2010 |
| WO | 2014037888 A1 | 3/2014 |
| WO | 2015077773 A1 | 5/2015 |
| WO | 2016122606 A1 | 8/2016 |
| WO | 2017100866 A1 | 6/2017 |
| WO | 2018035329 A1 | 2/2018 |
| WO | 2018144732 A1 | 8/2018 |
| WO | 2020172500 A1 | 8/2020 |

OTHER PUBLICATIONS

Mazanec et al., unpublished U.S. Appl. No. 17/006,467, entitled Programming of Cochlear Implant Accessories, filed Aug. 28, 2020, 74 pages.

* cited by examiner

COCHLEAR IMPLANT STIMULATION CALIBRATION

BACKGROUND

A cochlear implant is an electronic device that may be at least partially implanted surgically into the cochlea, the hearing organ of the inner ear, to provide improved hearing to a patient. Cochlear implants may include components that are worn externally by the patient and components that are implanted internally in the patient.

Cochlear implants may stimulate the cochlear tissue using electrical signals. Accuracy and precision of the electrical signals used to stimulate the cochlear nerve may be desired to ensure accurate and precise representations of sound. A lack of accuracy and precision of the electrical signals may not only lead to a lack of accuracy and precision of the representations of sound, but may also lead to undesired and unexpected charge accumulation within the tissue. This can cause damage to the cochlear tissue and/or implanted components. Cochlear implants may be calibrated before they are implanted internally in the patient, but may lose accuracy and precision after they have been implanted.

SUMMARY

Some aspects of the disclosure are generally directed toward cochlear implant systems. In some examples, a cochlear implant system can include a cochlear electrode comprising a plurality of contact electrode. The cochlear implant system can further include a stimulator in electrical communication with the cochlear electrode with the stimulator including a plurality of source element. Each of the plurality of source element can be in electrical communication with a corresponding one of the plurality of contact electrodes of the cochlear electrode. The cochlear implant system can further include an input source configured to receive a stimulus signal and generate an input signal based on the received stimulus signal. The cochlear implant system can also include a signal processor in communication with the stimulator and the input source with the signal processor being programmed with a transfer function and being configured to receive the input signal form the input source. The signal processor can output a stimulation signal to the stimulator based on the received input signal and the transfer function. The cochlear implant system can further include a testing circuit and a switching network with the switching network configured to selectively place each of the plurality of source elements into electrical communication with the testing circuit. The cochlear implant system can also include a controller in communication with the stimulator, the testing circuit, and the switching network. The controller can be configured to control the switching network to place one of the plurality of source element into communication with the testing circuit. The controller can further be configured to cause the stimulator to emit an electrical current from the one of the plurality of source elements in communication with the testing circuit. The controller can also be configured to determine an amount of electrical current emitted from the one of the plurality of source elements via the testing circuit. The controlled can also be configured to adjust the output of the one of the plurality of source element based on the determined amount of electrical current.

Some other aspects of the present disclosure are generally related to methods of calibrating current flow in a cochlear implant system. In some examples, a method of calibrating current flow in a cochlear implant system can include manipulating a switching network to position a first source element, corresponding to one of a plurality of contact electrodes of a cochlear electrode, into communication with a testing circuit. The method can further include providing an electrical current from the first source element to the testing circuit and determining an amount of electrical current provided by the first source element via the testing circuit. The method can also include adjusting the output of the first source element based on the determined amount of electrical current.

DETAILED DESCRIPTION

Figure 1:
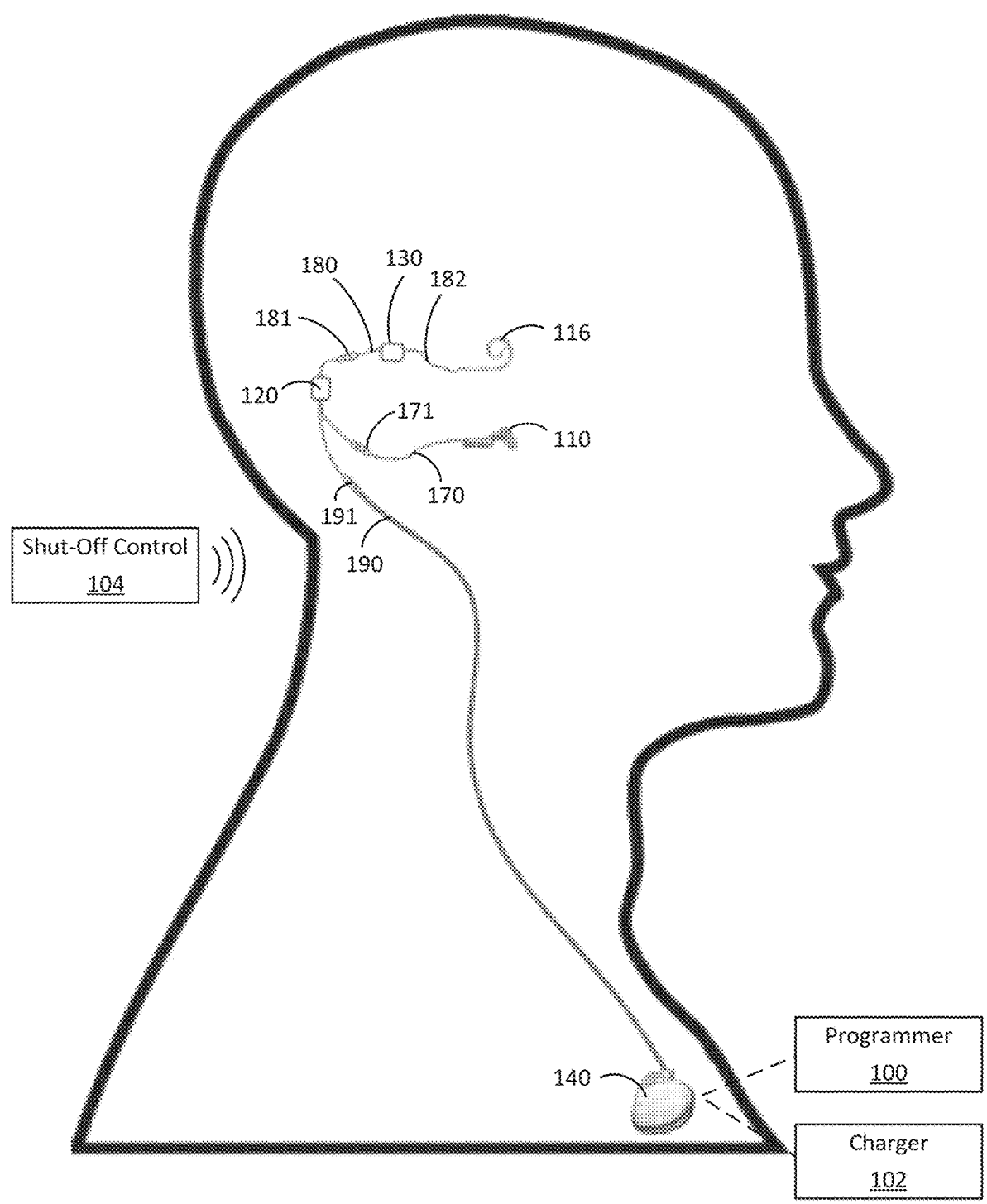
FIG. 1 shows a schematic illustration of a fully implantable cochlear implant system.

FIG. 1 shows a schematic illustration of a fully implantable cochlear implant system. The system of FIG. 1 includes a middle ear sensor 110 in communication with a signal processor 120. The middle ear sensor 110 can be configured to detect incoming sound waves, for example, using the ear structure of a patient. The signal processor 120 can be configured to receive a signal from the middle ear sensor 110 and produce an output signal based thereon. For example, the signal processor 120 can be programmed with instructions to output a certain signal based on a received signal. In some embodiments, the output of the signal processor 120 can be calculated using an equation based on received input signals. Alternatively, in some embodiments, the output of the signal processor 120 can be based on a lookup table or other programmed (e.g., in memory) correspondence between the input signal from the middle ear sensor 110 and the output signal. While not necessarily based explicitly on a function, the relationship between the input to the signal processor 120 (e.g., from the middle ear sensor 110) and the output of the signal processor 120 is referred to as the transfer function of the signal processor 120.

In various examples, the signal processor 120 can comprise any variety of components, for example, digital and/or analog processing components. In some embodiments, signal processor 120 comprises a digital signal processor, one or more microprocessors, microcontrollers, application specific integrated circuits (ASICs) or the like. Supporting circuitry for one or more such components can also be included as a part of the signal processor. In some embodiments, the signal processor can include or otherwise communicate with a memory containing programming for operating one or more components. Additionally or alternatively, in some embodiments, the signal processor can include one or more additional components. For example, in some embodiments, signal processor can include an embedded microphone or other sensor configured to detect incoming sound waves.

The system of FIG. 1 further includes a cochlear electrode 116 implanted into the cochlear tissues of a patient. The cochlear electrode 116 is in electrical communication with an electrical stimulator 130, which can be configured to provide electrical signals to the cochlear electrode 116 in response to input signals received by the electrical stimulator 130. In some examples, the cochlear electrode 116 is fixedly attached to the electrical stimulator 130. In other examples, the cochlear electrode 116 is removably attached to the electrical stimulator 130. As shown, the electrical stimulator 130 is in communication with the signal processor 120. In some embodiments, the electrical stimulator 130 provides electrical signals to the cochlear electrode 116 based on output signals from the signal processor 120.

In various embodiments, the cochlear electrode 116 can include any number of contact electrodes in electrical contact with different parts of the cochlear tissue. In such embodiments, the electrical stimulator 130 can be configured to provide electrical signals to any number of such contact electrodes to stimulate the cochlear tissue. For example, in some embodiments, the electrical stimulator 130 is configured to activate different contact electrodes or combinations of contact electrodes of the cochlear electrode 116 in response to different input signals received from the signal processor 120. This can help the patient differentiate between different input signals.

During exemplary operation, the middle ear sensor 110 detects audio signals, for example, using features of the patient's ear anatomy as described elsewhere herein and in U.S. Patent Publication No. 2013/0018216, which is hereby incorporated by reference in its entirety. The signal processor 120 can receive such signals from the middle ear sensor 110 and produce an output to the electrical stimulator 130 based on the transfer function of the signal processor 120. The electrical stimulator 130 can then stimulate one or more contact electrodes of the cochlear electrode 116 based on the received signals from the signal processor 120.

Figure 2:
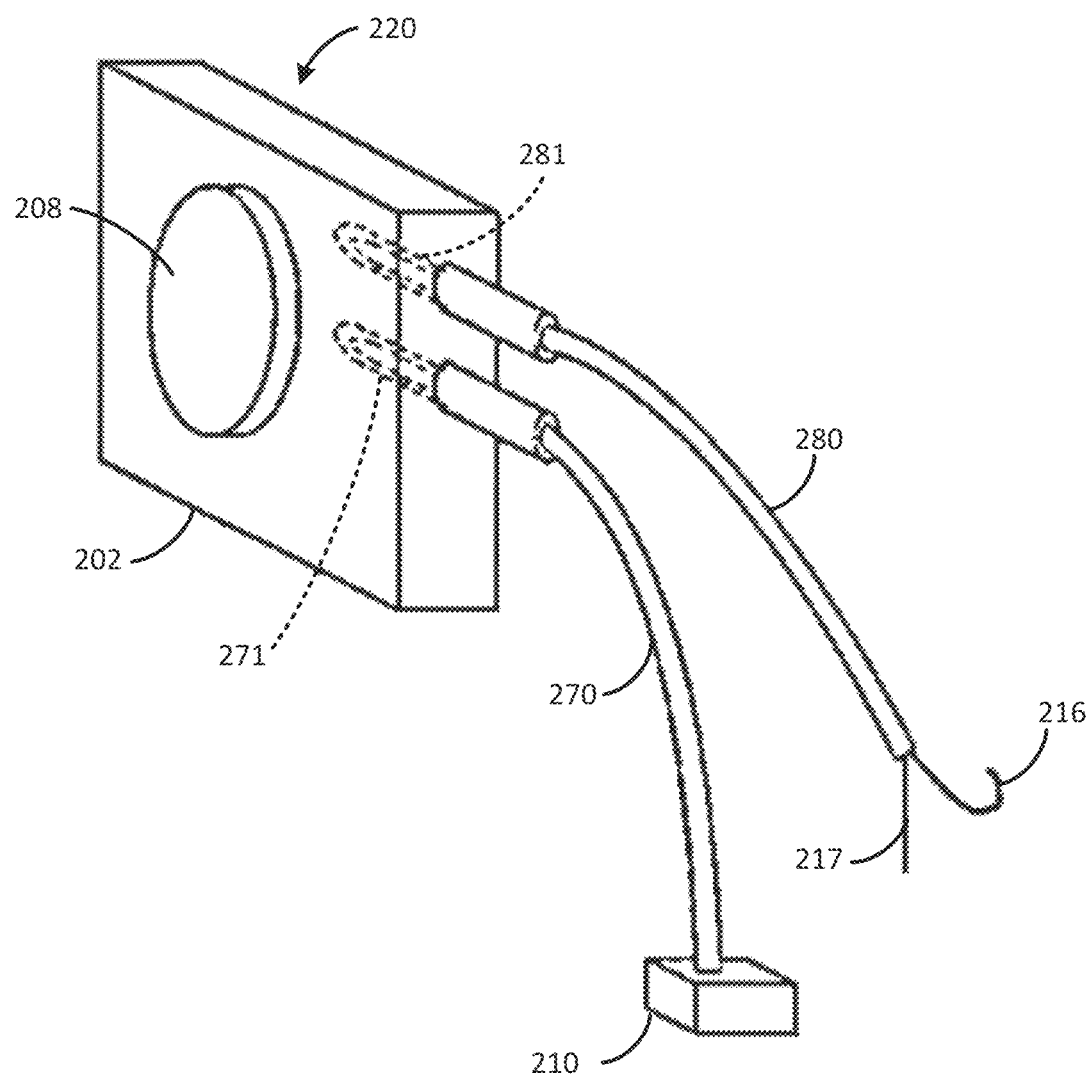
FIG. 2 shows an embodiment of a fully implantable cochlear implant.

Referring to FIG. 2, an embodiment of a fully-implantable cochlear implant is shown. The device in this embodiment includes a processor 220 (e.g., signal processor), a sensor 210, a first lead 270 connecting the sensor 210 to the processor 220, and a combination lead 280 attached to the processor 220, wherein combination lead 280 contains both a ground electrode 217 and a cochlear electrode 216. The illustrated processor 220 includes a housing 202, a coil 208, first female receptacle 271 and second female receptacle 281 for insertion of the leads 270 and 280, respectively.

In some embodiments, coil 208 can receive power and/or data from an external device, for instance, including a transmission coil (not shown). Some such examples are described in U.S. Patent Publication No. 2013/0018216, which is incorporated by reference. In other examples, processor 220 is configured to receive power and/or data from other sources, such as an implantable battery and/or communication module as shown in FIG. 1. Such battery and/or communication module can be implanted, for example, into the pectoral region of the patient in order to provide adequate room for larger equipment (e.g., a relatively large battery) for prolonged operation (e.g., longer battery life). Additionally, in the event a battery needs eventual replacement, a replacement procedure in the patient's pectoral region can be performed several times without certain vascularization issues that can arise near the location of the cochlear implant. For example, in some cases, repeated procedures (e.g., battery replacement) near the cochlear implant can result in a decreased ability for the skin in the region to heal after a procedure. Placing a replaceable component such as a battery in the pectoral region can facilitate replacement procedures with reduced risk for such issues.

Figure 3:
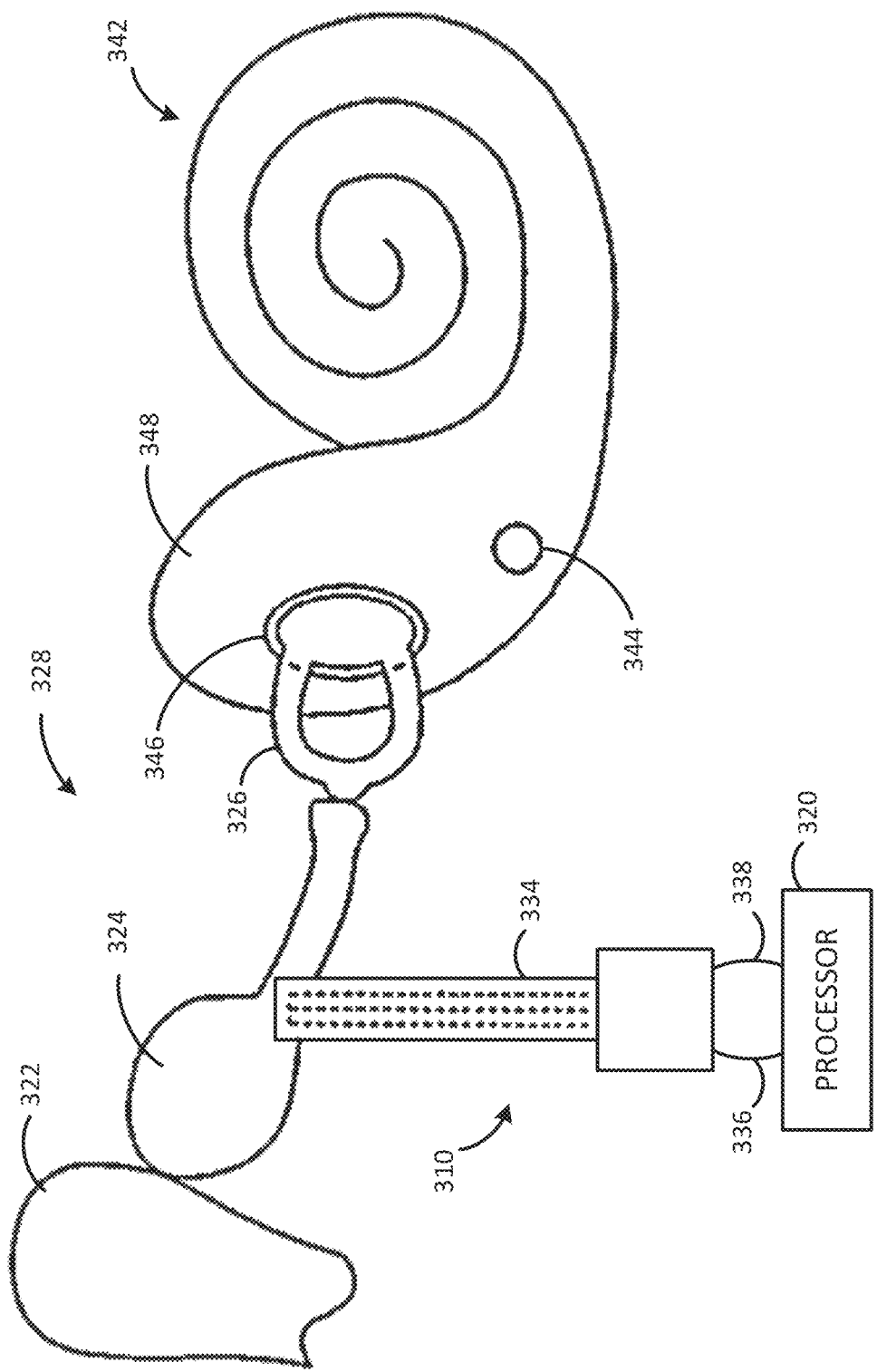
FIG. 3 illustrates an embodiments of an exemplary middle ear sensor for use in conjunction with anatomical features of a patient.

FIG. 3 illustrates embodiments of an exemplary middle ear sensor for use in conjunction with anatomical features of a patient. Referring to FIG. 3, an embodiment of the sensor 310 of a fully-implantable cochlear implant is shown. Also shown are portions of the subject's anatomy, which includes, if the subject is anatomically normal, at least the malleus 322, incus 324, and stapes 326 of the middle ear 328, and the cochlea 348, oval window 346, and round window 344 of the inner ear 342. Here, the sensor 310 is touching the incus 324. The sensor 310 can include a sensor such as described in U.S. Patent Publication No. 2013/0018216, which is incorporated by reference. Further, although not shown in a drawing, the sensor 310 may be in operative contact with the tympanic membrane or the stapes, or any combination of the tympanic membrane, malleus 322, incus 324, or stapes 326.

FIG. 3 illustrates an exemplary middle ear sensor for use with systems described herein. However, other middle ear sensors can be used, such as sensors using microphones or other sensors capable of receiving an input corresponding to detected sound and outputting a corresponding signal to the signal processor. Additionally or alternatively, systems can include other sensors configured to output a signal representative of sound received at or near a user's ear, such as a microphone or other acoustic pickup located in the user's outer ear or implanted under the user's skin. Such devices may function as an input source, for example, to the signal processor such that the signal processor receives an input signal from the input source and generates and output one or more stimulation signals according to the received input signal and the signal processor transfer function. Additionally or alternatively, systems can include other types of sensors, such as inner ear sensors. Some example configurations of such systems and other sensor arrangements are described in PCT patent application No. PCT/US20/19166, filed Feb. 21, 2020, which is assigned to the assignee of the instant application and is incorporated by reference.

Referring back to FIG. 1, the signal processor 120 is shown as being in communication with the middle ear sensor 110, the electrical stimulator 130, and the implantable battery and/or communication module 140. As described elsewhere herein, the signal processor 120 can receive input signals from the middle ear sensor 110 and/or other input source(s) and output signals to the electrical stimulator 130 for stimulating the cochlear electrode 116. The signal processor 120 can receive data (e.g., processing data establishing or updating the transfer function of the signal processor 120) and/or power from the implantable battery and/or communication module 140.

In some embodiments, the implantable battery and/or communication module 140 can communicate with one or more external components, such as a programmer 100 and/or a battery charger 102. The battery charger 102 can wirelessly charge the battery in the implantable battery and/or communication module 140 when brought into proximity with the implantable battery and/or communication module 140 in the pectoral region of the patient. Such charging can be accomplished, for example, using inductive charging. The programmer 100 can be configured to wirelessly communicate with the implantable battery and/or communication module 140 via any appropriate wireless communication technology, such as Bluetooth, Wi-Fi, and the like. In some examples, the programmer 100 can be used to update the system firmware and/or software. In an exemplary operation, the programmer 100 can be used to communicate an updated signal processor 120 transfer function to the implantable battery and/or communication module 140. In various embodiments, the programmer 100 and charger 102 can be separate devices or can be integrated into a single device.

In the illustrated example of FIG. 1, the signal processor 120 is connected to the middle ear sensor 110 via lead 170. In some embodiments, lead 170 can provide communication between the signal processor 120 and the middle ear sensor 110. In some embodiments, lead 170 can include a plurality of isolated conductors providing a plurality of communication channels between the middle ear sensor 110 and the signal processor 120. The lead 170 can include a coating such as an electrically insulating sheath to minimize any conduction of electrical signals to the body of the patient. In various embodiments, one or more communication leads can be detachable such that communication between two components can be disconnected in order to electrically and/or mechanically separate such components. For instance, in some embodiments, lead 170 includes a detachable connector 171. Detachable connector 171 can facilitate decoupling of the signal processor 120 and middle ear sensor 110. Example detachable connectors are described in PCT patent application No. PCT/US20/19166, which is incorporated by reference. For example, with reference to FIG. 1, in some embodiments, lead 170 can include a first lead extending from the middle ear sensor 110 having one of a male or a female connector and a second lead extending from the signal processor 120 having the other of the male or female connector. The first and second leads can be connected at detachable connector 171 in order to facilitate communication between the middle ear sensor 110 and the signal processor 120.

In other examples, a part of the detachable connector 171 can be integrated into one of the middle ear sensor 110 and the signal processor 120. For example, in an exemplary embodiment, the signal processor 120 can include a female connector integrated into a housing of the signal processor 120. Lead 170 can extend fully from the middle ear sensor 110 and terminate at a corresponding male connector for inserting into the female connector of the signal processor 120. In still further embodiments, a lead (e.g., 170) can include connectors on each end configured to detachably connect with connectors integrated into each of the components in communication. For example, lead 170 can include two male connectors, two female connectors, or one male and one female connector for detachably connecting with corresponding connectors integral to the middle ear sensor 110 and the signal processor 120. Thus, lead 170 may include two or more detachable connectors.

Similar communication configurations can be established for detachable connector 181 of lead 180 facilitating communication between the signal processor 120 and the stimulator 130 and for detachable connector 191 of lead 190 facilitating communication between the signal processor 120 and the implantable battery and/or communication module 140. Leads (170, 180, 190) can include pairs of leads having corresponding connectors extending from each piece of communicating equipment, or connectors can be built in to any one or more communicating components.

In such configurations, each of the electrical stimulator 130, signal processor 120, middle ear sensor 110, and battery and/or communication module can each be enclosed in a housing, such as a hermetically sealed housing comprising biocompatible materials. Such components can include feedthroughs providing communication to internal components enclosed in the housing. Feedthroughs can provide electrical communication to the component via leads extending from the housing and/or connectors integrated into the components.

In a module configuration such as that shown in FIG. 1, various components can be accessed (e.g., for upgrades, repair, replacement, etc.) individually from other components. For example, as signal processor 120 technology improves (e.g., improvements in size, processing speed, power consumption, etc.), the signal processor 120 implanted as part of the system can be removed and replaced independently of other components. In an exemplary procedure, an implanted signal processor 120 can be disconnected from the electrical stimulator 130 by disconnecting detachable connector 181, from the middle ear sensor 110 by disconnecting detachable connector 171, and from the implantable battery and/or communication module 140 by disconnecting detachable connector 191. Thus, the signal processor 120 can be removed from the patient while other components such as the electrical stimulator 130, cochlear electrode 116, middle ear sensor 110, and battery and/or communication module can remain in place in the patient.

After the old signal processor is removed, a new signal processor can be connected to the electrical stimulator 130, middle ear sensor 110, and implantable battery and/or communication module 140 via detachable connectors 181, 171, and 191, respectively. Thus, the signal processor (e.g., 120) can be replaced, repaired, upgraded, or any combination thereof, without affecting the other system components. This can reduce, among other things, the risk, complexity, duration, and recovery time of such a procedure. In particular, the cochlear electrode 116 can be left in place in the patient's cochlea while other system components can be adjusted, reducing trauma to the patient's cochlear tissue.

Such modularity of system components can be particularly advantageous when replacing a signal processor 120, such as described above. Processor technology continues to improve and will likely continue to markedly improve in the future, making the signal processor 120 a likely candidate for significant upgrades and/or replacement during the patient's lifetime. Additionally, in embodiments such as the embodiment shown in FIG. 1, the signal processor 120 communicates with many system components. For example, as shown, the signal processor 120 is in communication with each of the electrical stimulator 130, the middle ear sensor 110, and the implantable battery and/or communication module 140. Detachably connecting such components with the signal processor 120 (e.g., via detachable connectors 181, 171, and 191) enables replacement of the signal processor 120 without disturbing any other components. Thus, in the event of an available signal processor 120 upgrade and/or a failure of the signal processor 120, the signal processor 120 can be disconnected from other system components and removed.

While many advantages exist for a replaceable signal processor 120, the modularity of other system components can be similarly advantageous, for example, for upgrading any system component. Similarly, if a system component (e.g., the middle ear sensor 110) should fail, the component can be disconnected from the rest of the system (e.g., via detachable connector 171) and replaced without disturbing the remaining system components. In another example, even a rechargeable battery included in the implantable battery and/or communication module 140 may eventually wear out and need replacement. The implantable battery and/or communication module 140 can be replaced or accessed (e.g., for replacing the battery) without disturbing other system components. Further, as discussed elsewhere herein, when the implantable battery and/or communication module 140 is implanted in the pectoral region of the patient, such as in the illustrated example, such a procedure can leave the patient's head untouched, eliminating unnecessarily frequent access beneath the skin.

While various components are described herein as being detachable, in various embodiments, one or more components configured to communicate with one another can be integrated into a single housing. For example, in some embodiments, signal processor 120 can be integrally formed with the stimulator 130 and cochlear electrode 116. For example, in an exemplary embodiment, processing and stimulation circuitry of a signal processor 120 and stimulator 130 can be integrally formed as a single unit in a housing coupled to a cochlear electrode. Cochlear electrode and the signal processor/stimulator can be implanted during an initial procedure and operate as a single unit.

In some embodiments, while the integral signal processor/stimulator/cochlear electrode component does not get removed from a patient due to potential damage to the cochlear tissue into which the cochlear electrode is implanted, system upgrades are still possible. For example, in some embodiments, a modular signal processor may be implanted alongside the integral signal processor/stimulator component and communicate therewith. In some such examples, the integral signal processor may include a built-in bypass to allow a later-implanted signal processor to interface directly with the stimulator. Additionally or alternatively, the modular signal processor can communicate with the integral signal processor, which may be programmed with a unity transfer function. Thus, in some such embodiments, signals from the modular signal processor may be essentially passed through the integral signal processor unchanged so that the modular signal processor effectively controls action of the integral stimulator. Thus, in various embodiments, hardware and/or software solutions exist for upgrading an integrally attached signal processor that may be difficult or dangerous to remove.

While often described herein as using an electrical stimulator to stimulate the patient's cochlear tissue via a cochlear electrode, in some examples, the system can additionally or alternatively include an acoustic stimulator. An acoustic stimulator can include, for example, a transducer (e.g., a piezoelectric transducer) configured to provide mechanical stimulation to the patient's ear structure. In an exemplary embodiment, the acoustic stimulator can be configured to stimulate one or more portions of the patient's ossicular chain via amplified vibrations. Acoustic stimulators can include any appropriate acoustic stimulators, such as those found in the ESTEEM™ implant (Envoy Medical Corp., St. Paul, Minn.) or as described in U.S. Pat. Nos. 4,729,366, 4,850,962, and 7,524,278, and U.S. Patent Publication No. 20100042183, each of which is incorporated herein by reference in its entirety.

Figure 4:
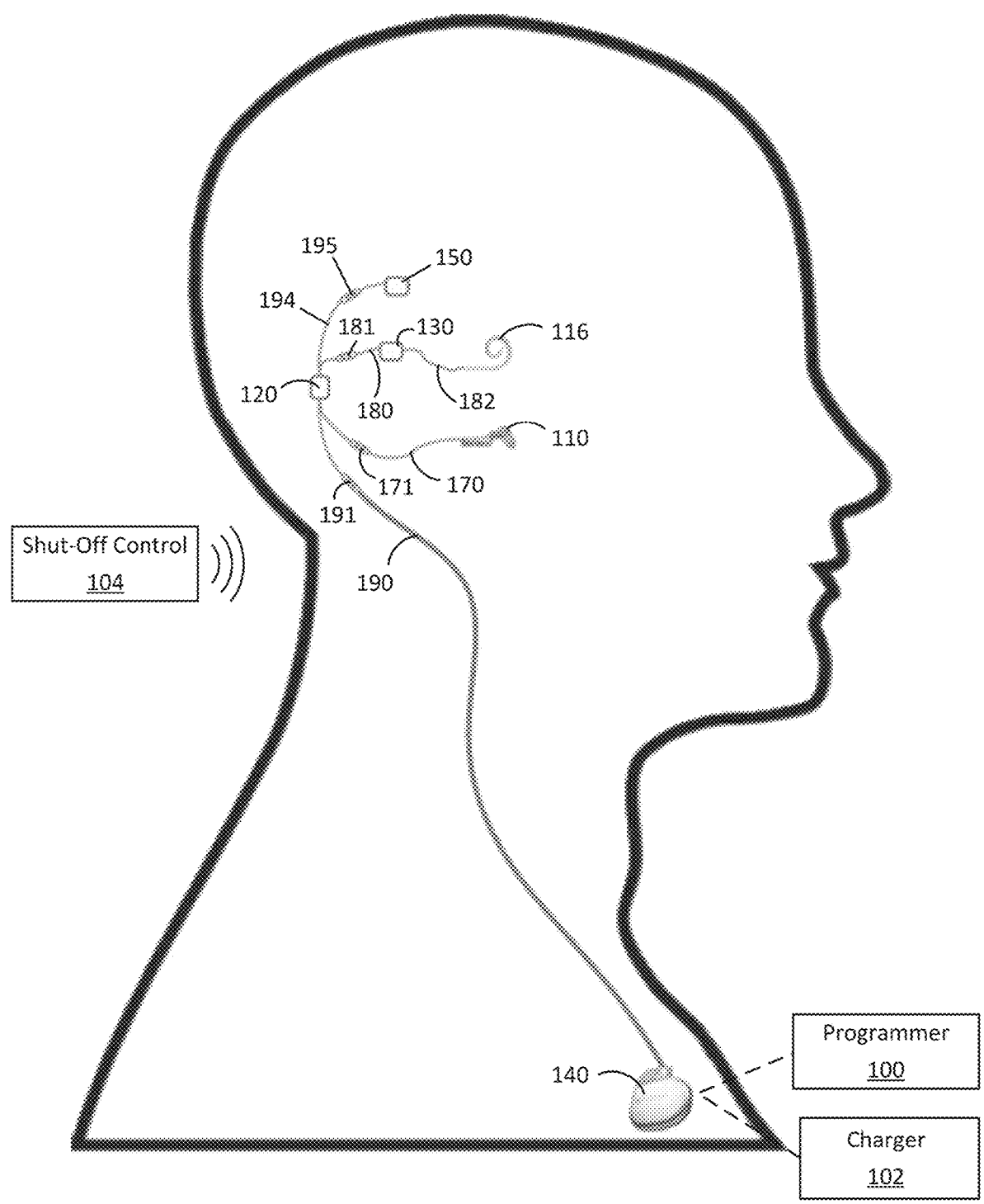
FIG. 4 is a schematic diagram illustrating an exemplary implantable system including an acoustic stimulator.

FIG. 4 is a schematic diagram illustrating an exemplary implantable system including an acoustic stimulator. The acoustic stimulator can be implanted proximate the patient's ossicular chain and can be in communication with a signal processor via lead 194 and detachable connector 195. The signal processor can behave as described elsewhere herein and can be configured to cause acoustic stimulation of the ossicular chain via the acoustic stimulator in in response to input signals from the middle ear sensor according to a transfer function of the signal processor.

The acoustic stimulator of FIG. 4 can be used similarly to the electrical stimulator as described elsewhere herein. For instance, an acoustic stimulator can be mechanically coupled to a patient's ossicular chain upon implanting the system and coupled to the signal processor via lead 194 and detachable connector 195. Similarly to systems described elsewhere herein with respect to the electrical stimulator, if the signal processor requires replacement or repair, the signal processor can be disconnected from the acoustic stimulator (via detachable connector 195) so that the signal processor can be removed without disturbing the acoustic stimulator.

In general, systems incorporating an acoustic stimulator such as shown in FIG. 4 can operate in the same way as systems described elsewhere herein employing an electrical stimulator and cochlear electrode only substituting electrical stimulation for acoustic stimulation.

Some systems can include a hybrid system comprising both an electrical stimulator and an acoustic stimulator in communication with the signal processor. In some such examples, the signal processor can be configured to stimulate electrically and/or acoustically according to the transfer function of the signal processor. In some examples, the type of stimulation used can depend on the input signal received by the signal processor. For instance, in an exemplary embodiment, the frequency content of the input signal to the signal processor can dictate the type of stimulation. In some cases, frequencies below a threshold frequency could be represented using one of electrical and acoustic stimulation while frequencies above the threshold frequency could be represented using the other of electrical and acoustic stimulation. Such a threshold frequency could be adjustable based on the hearing profile of the patient. Using a limited range of frequencies can reduce the number of frequency domains, and thus the number of contact electrodes, on the cochlear electrode. In other examples, rather than a single threshold frequency defining which frequencies are stimulated electrically and acoustically, various frequencies can be stimulated both electrically and acoustically. In some such examples, the relative amount of electrical and acoustic stimulation can be frequency-dependent. As described elsewhere herein, the signal processor transfer function can be updated to meet the needs of the patient, including the electrical and acoustic stimulation profiles.

Additionally or alternatively, while many examples show a middle ear sensor being in communication with an implanted signal processor, in various embodiments, one or more additional or alternative input sources can be included. For instance, in some embodiments, a microphone can be implanted under a user's skin and can be placed in communication with the signal processor (e.g., via a detachable connector such as 171). The signal processor can receive input signals from the implanted microphone and provide signals to the stimulator based on the received input signal and the signal processor transfer function. Additionally or alternatively, systems can include a middle ear sensor as an input source, wherein the middle ear sensor is configured to detect stimuli (e.g., pressure signals) from the wearer's inner ear (e.g., within the cochlear tissue).

With further reference to FIGS. 1 and 4, in some examples, a system can include a shut-off controller 104, which can be configured to wirelessly stop an electrical stimulator 130 from stimulating the patient's cochlear tissue and/or an acoustic stimulator 150 from stimulating the patient's ossicular chain. For example, if the system is malfunctioning or an uncomfortably loud input sound causes an undesirable level of stimulation, the user may use the shut-off controller 104 to cease stimulation from the stimulator 130. The shut-off controller 104 can be embodied in a variety of ways. For example, in some embodiments, the shut-off controller 104 can be integrated into other external components, such as the programmer 100. In some such examples, the programmer 100 includes a user interface by which a user can select an emergency shut-off feature to cease stimulation. Additionally or alternatively, the shut-off controller 104 can be embodied as a separate component. This can be useful in situations in which the patient may not have immediate access to the programmer 100. For example, the shut-off controller 104 can be implemented as a wearable component that the patient can wear at all or most times, such as a ring, bracelet, necklace, or the like.

The shut-off controller 104 can communicate with the system in order to stop stimulation in a variety of ways. In some examples, the shut-off controller 104 comprises a magnet that is detectable by a sensor (e.g., a Hall-Effect sensor) implanted in the patient, such as in the processor and/or the implantable battery and/or communication module 140. In some such embodiments, when the magnet is brought sufficiently close to the sensor, the system can stop stimulation of the cochlear tissue or ossicular chain.

After the shut-off controller 104 is used to disable stimulation, stimulation can be re-enabled in one or more of a variety of ways. For example, in some embodiments, stimulation is re-enabled after a predetermined amount of time after it had been disabled. In other examples, the shut-off controller 104 can be used to re-enable stimulation. In some such examples, the patient brings the shut-off controller 104 within a first distance of a sensor (e.g., a magnetic sensor) to disable stimulation, and then removes the shut-off controller 104. Subsequently, once the patient brings the shut-off controller 104 within a second distance of the sensor, stimulation can be re-enabled. In various embodiments, the first distance can be less than the second distance, equal to the second distance, or greater than the second distance. In still further embodiments, another device such as a separate turn-on controller (not shown) or the programmer 100 can be used to re-enable stimulation. Any combination of such re-enabling of stimulation can be used, such as alternatively using either the programmer 100 or the shut-off controller 104 to enable stimulation or combining a minimum "off" time before any other methods can be used to re-enable stimulation.

In some embodiments, rather than entirely disable stimulation, other actions can be taken, such as reducing the magnitude of stimulation. For example, in some embodiments, the shut-off sensor can be used to reduce the signal output by a predetermined amount (e.g., absolute amount, percentage, etc.). In other examples, the shut-off sensor can affect the transfer function of the signal processor to reduce the magnitude of stimulation in a customized way, such as according to frequency or other parameter of an input signal (e.g., from the middle ear sensor).

In some examples, implantable battery and/or communication module can be used to provide power and/or data (e.g., processing instructions) to other system components via lead 190. Different challenges exist for communicating electrical signals through a patient's body. For example, safety standards can limit the amount of current that can safely flow through a patient's body (particularly DC current). Additionally, the patient's body can act as an undesired signal path from component to component (e.g., via contact with the housing or "can" of each component).

Figure 5A:
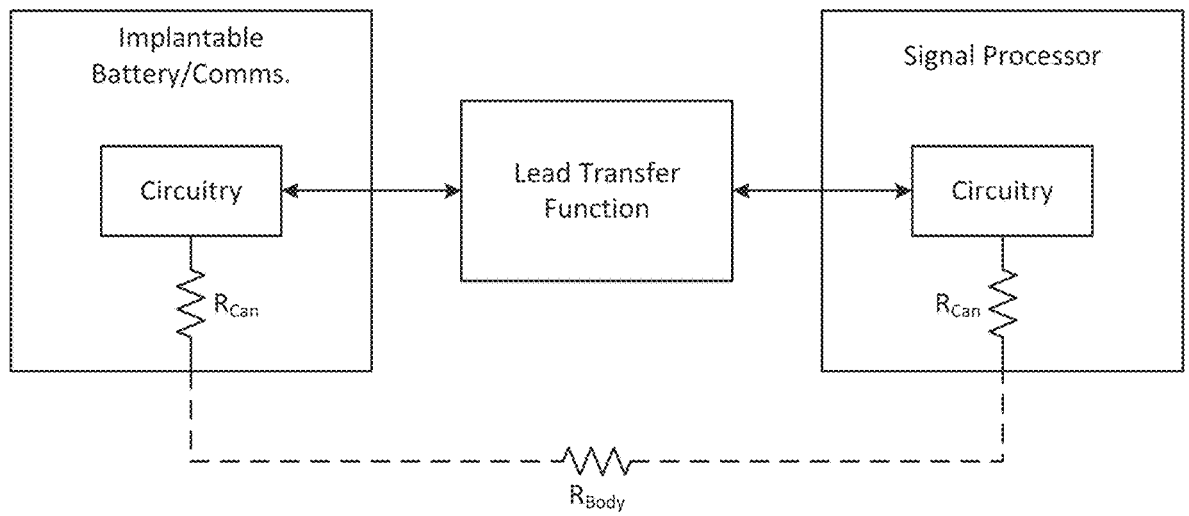
FIG. 5A is a high-level electrical schematic showing communication between the implantable battery and/or communication module and the signal processor.

FIG. 5A is a high-level electrical schematic showing communication between the implantable battery and/or communication module and the signal processor. In the illustrated embodiment, the implantable battery and/or communication module includes circuitry in communication with circuitry in the signal processor. Communication between the circuitry in the implantable battery and/or communication module and the signal processor can be facilitated by a lead (190), represented by the lead transfer function. The lead transfer function can include, for example, parasitic resistances and capacitances between the leads connecting the implantable battery and/or communication module and the signal processor and the patient's body and/or between two or more conductors that make up the lead (e.g., 191). Signals communicated from the circuitry of the implantable battery and/or communication module to the circuitry in the signal processor can include electrical power provided to operate and/or stimulate system components (e.g., the middle ear sensor, signal processor, electrical and/or acoustic stimulator, and/or cochlear electrode) and/or data (e.g., processing data regarding the transfer function of the signal processor).

Various systems and methods can be employed provide communication between system components. Some examples of possible communication techniques are described in PCT patent application No. PCT/US20/19166, which is incorporated by reference. In some examples, data can be communicated to the implantable battery and/or communication module from an external component, such as a programmer as shown in FIG. 1. In an exemplary process, a programmer, such as a clinician's computer, can be used to communicate with a patient's fully implanted system via the implantable battery and/or communication module, which can communicate information to other system components, such as via lead 190.

During such processes, a clinician can communicate with the signal processor, and, in some cases, with other components via the signal processor. For example, the clinician can cause the signal processor to actuate an electrical and/or an acoustic stimulator in various ways, such as using various electrical stimulation parameters, combinations of active contact electrodes, various acoustic stimulation parameters, and various combinations thereof. Varying the stimulation parameters in real time can allow the clinician and patient to determine effectiveness of different stimulation techniques for the individual patient. Similarly, the clinician can communicate with the signal processor to update transfer function. For example, the clinician can repeatedly update the transfer function signal processor while testing the efficacy of each one on the individual patient. In some examples, combinations of stimulation parameters and signal processor transfer functions can be tested for customized system behavior for the individual patient.

In some embodiments, various internal properties of the system may be tested. For instance, various impedance values, such as a sensor impedance or a stimulator impedance can be tested such as described in U.S. Patent Publication No. 2015/0256945, entitled TRANSDUCER IMPEDANCE MEASUREMENT FOR HEARING AID, which is assigned to the assignee of the instant application, the relevant portions of which are incorporated by reference herein.

As discussed elsewhere herein, the body of the patient provides an electrical path between system components, such as the "can" of the implantable battery and/or communication module and the "can" of the signal processor. This path is represented in FIG. 5A by the flow path through $R_{Body}$. Thus, the patient's body can provide undesirable signal paths which can negatively impact communication between components. To address this, in some embodiments, operating circuitry in each component can be substantially isolated from the component "can" and thus the patient's body. For example, as shown, resistance $R_{Can}$ is positioned between the circuitry and the "can" of both the implantable battery and/or communication module and the signal processor.

While being shown as $R_{Can}$ in each of the implantable battery and/or communication module and the signal processor, it will be appreciated that the actual value of the resistance between the circuitry and respective "can" of different elements is not necessarily equal. Additionally, $R_{Can}$ need not include purely a resistance, but can include other components, such as one or more capacitors, inductors, and the like. That is, $R_{Can}$ can represent an insulating circuit including any variety of components that act to increase the impedance between circuitry within a component and the "can" of the component. Thus, $R_{Can}$ can represent an impedance between the operating circuitry of a component and the respective "can" and the patient's tissue. Isolating the circuitry from the "can" and the patient's body acts to similarly isolate the circuitry from the "can" of other components, allowing each component to operate with reference to a substantially isolated component ground. This can eliminate undesired communication and interference between system components and/or between system components and the patient's body.

Figure 5B:
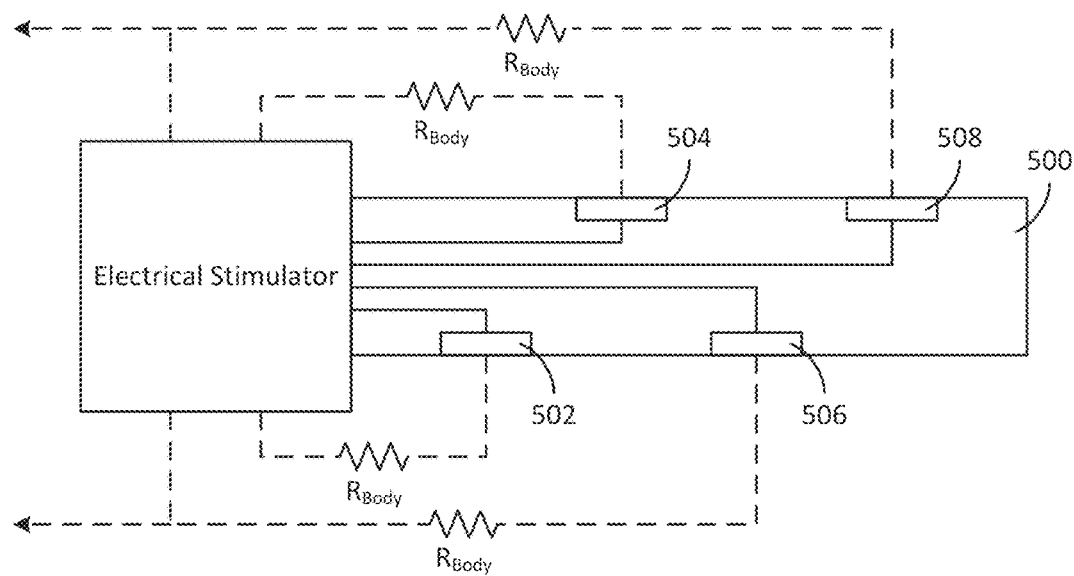
FIG. 5B illustrates an exemplary schematic diagram illustrating a cochlear electrode having a plurality of contact electrodes and fixedly or detachably connected to an electrical stimulator.

For example, as described elsewhere herein, in some examples, an electrical stimulator can provide an electrical stimulus to one or more contact electrodes on a cochlear electrode implanted in a patient's cochlear tissue. FIG. 5B illustrates an exemplary schematic diagram illustrating a cochlear electrode having a plurality of contact electrodes and fixedly or detachably connected to an electrical stimulator. As shown, the cochlear electrode 500 has four contact electrodes 502, 504, 506, and 508, though it will be appreciated that any number of contact electrodes is possible. As described elsewhere herein, the electrical stimulator can provide electrical signals to one or more such contact electrodes in response to an output from the signal processor according to the transfer function thereof and a received input signal.

Because each contact electrode 502-1008 is in contact with the patient's cochlear tissue, each is separated from the "can" of the electrical stimulator (as well as the "cans" of other system components) via the impedance of the patient's tissue, shown as $R_{Body}$. Thus, if the circuitry within various system components did not have sufficiently high impedance (e.g., $R_{Can}$) to the component "can", electrical signals may stimulate undesired regions of the patient's cochlear tissue. For instance, stimulation intended for a particular contact electrode (e.g., 502) may lead to undesired stimulation of other contact electrodes (e.g., 504, 506, 508), reducing the overall efficacy of the system. Minimizing the conductive paths between system components (e.g., to the contact electrodes of a cochlear electrode) due to the patient's body, such as by incorporating impedances between component circuitry and the corresponding "can" via $R_{Can}$, can therefore improve the ability to apply an electrical stimulus to only a desired portion of the patient's body.

It will be appreciated that the term $R_{Body}$ is used herein to generally represent the resistance and/or impedance of the patient's tissue between various components and does not refer to a specific value. Moreover, each depiction or $R_{Body}$ in the figures does not necessarily represent the same value of resistance and/or impedance as the others.

Figure 6A:
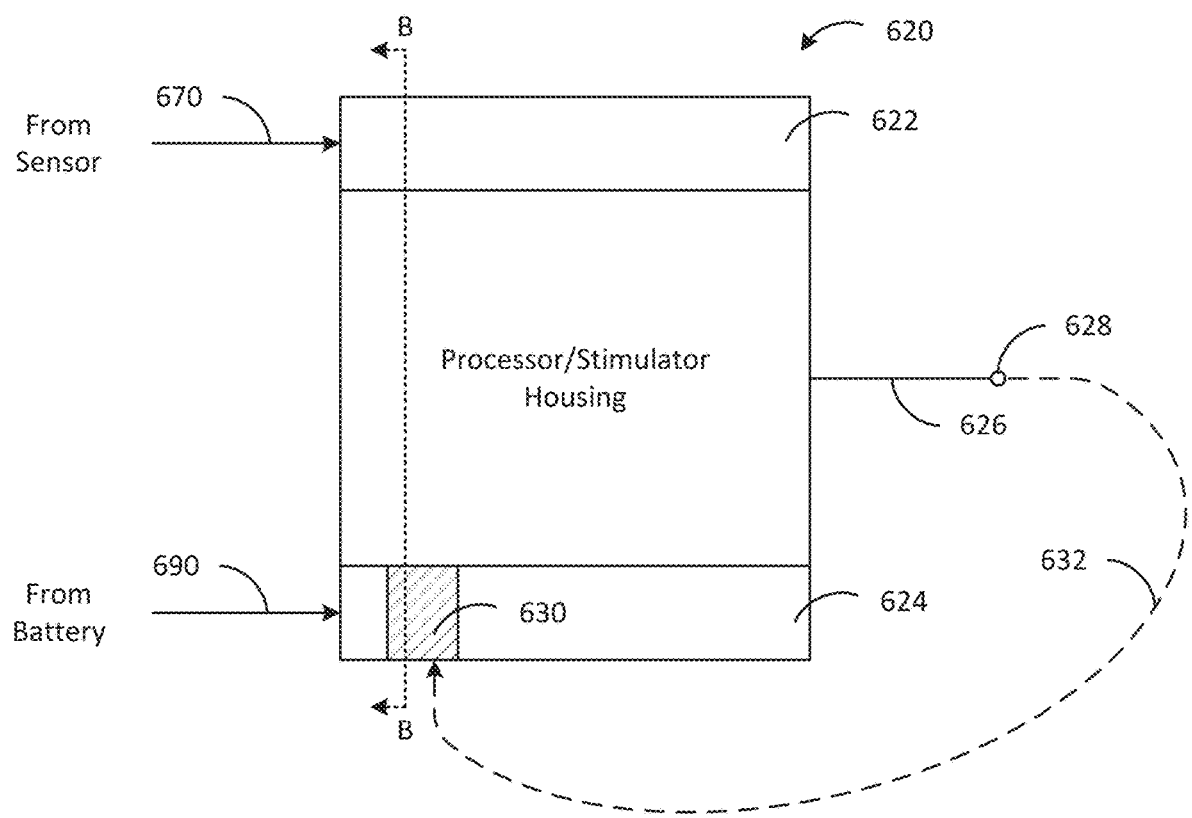
FIG. 6A shows an exemplary schematic illustration of processor and stimulator combined into a single housing.

While shown in several embodiments (e.g., FIGS. 1 and 4) as being separate components connected by a lead (e.g., lead 180), in some examples, the processor (e.g., 120) and the stimulator (e.g., 130) can be integrated into a single component, for example, within a hermetically sealed housing. FIG. 6A shows an exemplary schematic illustration of processor and stimulator combined into a single housing. In the example of FIG. 6A, the processor/stimulator 620 receives signal inputs from the sensor (e.g., a middle ear sensor) via lead 670 and power from a battery (e.g., the implantable battery and/or communication module) via lead 690. The processor/stimulator 620 can include headers 622, 624 for receiving leads 670, 690, respectively.

The processor/stimulator 620 can be configured to receive an input signal from the sensor, process the received input signal according to a transfer function, and output a stimulation signal via electrode 626. Electrode 626 can include one or more contact electrodes (e.g., 628) in contact with a wearer's cochlear tissue to provide electrical stimulation thereto, for example, as described with respect to FIG. 5B.

The processor/stimulator 620 of FIG. 6 includes a return electrode 630 for providing a return path (e.g., 632) for stimulation signals emitted from electrode 626. The return electrode 630 can be electrically coupled to a ground portion of circuitry within the processor/stimulator 620 to complete a circuit comprising circuitry within the processor/stimulator 620, the electrode 626, the wearer's cochlear tissue, and ground. In some examples, the return electrode 630 comprises an electrically conductive material in electrical communication with circuitry inside the processor/stimulator 620, while the rest of the housing of the processor/stimulator 620 is generally not electrically coupled to internal circuitry.

In some embodiments, the return electrode 630 and the housing of the processor/stimulator 620 comprise electrically conductive materials. For instance, in some examples, the housing comprises titanium while the return electrode 630 comprises platinum or a platinum alloy. Header 624 can generally include a non-conductive biocompatible material, such as a biocompatible polymer. The non-conductive header 624 can provide isolation between the return electrode 630 and the conductive housing of the processor/stimulator 620.

While shown in FIG. 6A as being positioned in the power header 624 of the processor/stimulator 620, in general, the return electrode 630 can be positioned anywhere on the exterior surface of the processor/stimulator 620. In some examples, one or more redundant return electrodes can be included, for example, at or near the interface of the housing and the electrode 626. In some examples, a return electrode can be positioned on a proximal end of the electrode 626 itself. In some embodiments having a plurality of return electrodes (e.g., return electrode 630 and a return electrode on the proximal end of electrode 626), a switch can be used to select which return electrode is used. Additionally or alternatively, a plurality of return electrodes can be used simultaneously.

Figure 6B:
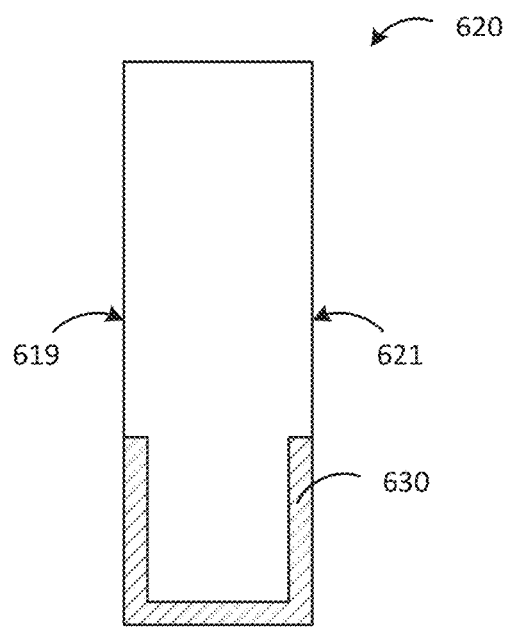
FIG. 6B shows a simplified cross-sectional view of the processor/stimulator shown in FIG. 6A taken along lines B-B.

FIG. 6B shows a simplified cross-sectional view of the processor/stimulator shown in FIG. 6A taken along lines B-B. As shown in FIG. 6B, processor/stimulator 620 includes a housing having a first side 619 and a second side 621 and a return electrode 630 embedded in the housing. Return electrode 630 can comprise a conductive material suitable for contact with a wearer's tissue, such as platinum. In the illustrated example, the return electrode 630 wraps around to both sides of the housing of the processor/stimulator 620 so that the return electrode 630 is coupled to the outer surface of the housing on the first side 619 and the second side 621.

This can facilitate implanting onto either side of a wearer's anatomy, since in some cases, only one side of the processor/stimulator electrically contacts conductive tissue of the wearer while the other side contacts, for instance, the skull of the wearer, and does not easily provide the return path (e.g., 632). Thus, a single processor/stimulator design can be implanted in either side of a wearer's anatomy while providing an adequate return path via a return electrode 630.

In various examples, the return electrode 630 can extend around a perimeter edge of the processor/stimulator 620, as shown in FIG. 6B. In other examples, the return electrode 630 can include sections on either side of the housing and can be connected to one another internally within the housing rather than via a wrap-around contact. Additionally, while shown as being embedded in the housing of the processor/stimulator 620, in some examples, return electrode 630 can protrude outwardly from the housing. Return electrode 630 can generally be any of a variety of shapes and sizes while including an electrical contact section on opposing sides of the housing to provide usability on either side of a wearer's anatomy. In other embodiments, return electrode can be positioned only one side of the housing for a customized right-side or left-side implementation.

As described elsewhere herein, in various embodiments, the processor generally receives an input signal, processes the signal, and generates a stimulation signal, which can be applied via an integrated stimulator (e.g., via a processor/stimulator such as in FIGS. 6A and 6B) or a separate stimulator in communication with the processor (e.g., as shown in FIGS. 1 and 4). In some such embodiments, the input signal received via the signal processor is generated by an implantable sensor, such as a middle ear sensor (e.g., as described with respect to FIGS. 4 and 5).

However, such sensors often measure or otherwise receive some stimulus that is converted into an output that is read and processed by the signal processor. For example, some middle ear sensors may produce a different output signal for a given stimulus depending on a variety of factors, such as variability in a wearer's inner-ear anatomy and motion. Thus, the output of a sensor for a given input may be not predictable while designing a system, especially across a range of frequencies and/or magnitudes.

It can be desirable to ensure the applied stimulation signal is a correct interpretation of a prescribed signal for accuracy and safety reasons. For example, for a given prescribed current to be applied via an electrode, the actual applied current may depart from the prescribed current. This can be due to various factors, such as electronics imprecisely calibrated, the behavior of electronics over time, and variability driven mismatches between various electronic components. However, it can be desirable to ensure electrical pulses generated by the cochlear implant system are charge-balanced. Charge-balanced means that the amount of charge sourced to the wearer's tissue is the same amount of charge sunk as delivered from the tissue over time. For example, to balance charge applied to patient tissue, a first current (e.g., in the form of pulses) put into the tissue via contact electrodes for an amount of time would be the same magnitude as a second current taken out of the tissue via the contact electrodes for the same amount of time. Discrepancies between a prescribed current that the system believes is being sourced/sunk and the actual current being sourced/sunk can result in unexpected and undetected charge accumulation over time. Such charge accumulation can cause damage to the wearer's tissue and/or the implanted electronics and/or the deterioration of the interface between the electrode and the tissue and/or fluid.

Figure 7A:
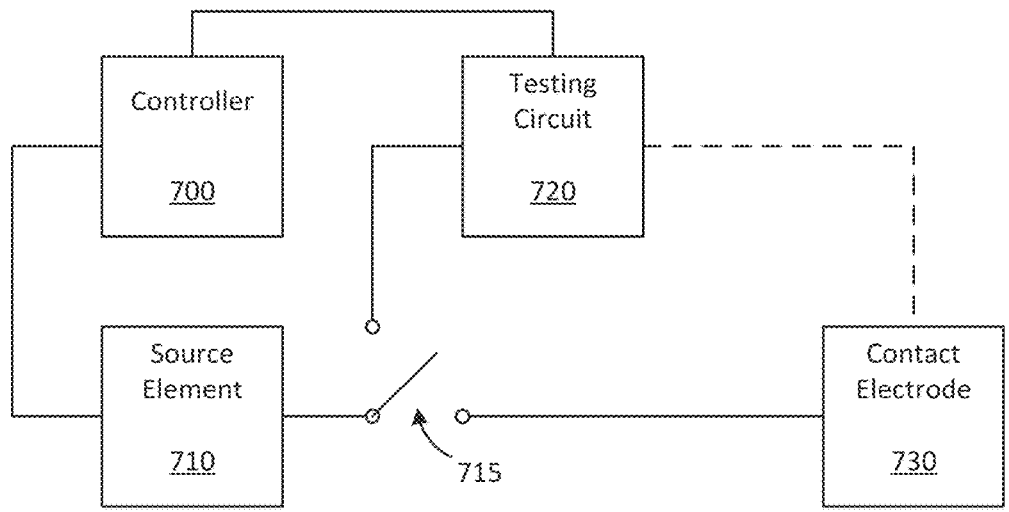
FIG. 7A is a high-level electrical schematic showing communications between various components of a cochlear implant system for a single contact electrode including a testing circuit.

FIG. 7A is a high-level electrical schematic showing communications between a source element 710, a switch 715, a controller 700, a testing circuit 720, and a contact electrode 730. In the illustrated embodiment, the switch 715 can selectively connect the source element 710 with either of the testing circuit 720 or the contact electrode 730. By connecting the source element 710 to either the testing circuit 720 or the contact electrode, current can flow from the source element 710 to either of the testing circuit 720 or the contact electrode 730. As shown by the broken line in FIG. 7A, in some embodiments, a current can flow through the testing circuit 720 and to the contact electrode 730. The switch 715 can be any type of switch (e.g. transistor), and in some examples more than one switch can be used. In some embodiments, the switch 715 is controlled by the controller 700.

In various examples, controller 700 includes one or more processors, such as one or more digital signal processors and/or microprocessors. Additionally or alternatively, controller 700 can include one or more microcontrollers, application specific integrated circuits (ASICs) or the like. In some embodiments, the controller 700 can include or otherwise communicate with a memory containing programming for operating one or more components.

In some examples, source element 710 of FIG. 7A can include a current source and/or a current sink. As a current source, the source element 710 can provide (e.g. source) a current to contact electrode 730 and/or testing circuit 720. As a current sink, the source element 710 can receive (e.g. sink) current which has traveled through the contact electrode and/or the testing circuit. Current sources and/or sinks can be provided via, for example, one or more current source or sink integrated circuits or other appropriate arrangement of one or more components configured to source or sink current as would be understood by a person having ordinary skill in the art. In various embodiments, source element 710 can source or sink current, for example, as prescribed by controller 700, which can provide a signal to the source element 710 to control an amount of current sourced or sunk thereby. Unless specified otherwise, descriptions of embodiments herein in which a source element (e.g., 710) provides a current (e.g., to contact electrode 730) can similarly describe times or embodiments in which a source element sinks current. In various examples, a source element (e.g., 710) can "provide" positive or negative current to a contact electrode, acting as a current source or a sink.

In some embodiments, current can originate from a power source and ultimately return to the power source using the source element 710 as a current source and/or current sink. In some such embodiments, a circuit is formed where current flows from the power source through the source element 710, through to the contact electrode 730 and/or testing circuit 720, back through the source element 710, and back to the power source. During example stimulation, current from the source element 710 can flow through contract electrode 730 via switch 715, through a wearer's tissue, and return to a return electrode (e.g., return electrode 630 via path 632 in FIG. 6).

As described elsewhere herein, the source element 710 can be included as part of a stimulator (e.g. 130 and 150). In some embodiments, the source element 710 comprises a digital to analog converter (DAC) which can convert digital signals to analog signals. For example, in FIG. 7A, the source element 710 is in communication with controller 700. In some examples, controller 700 is part of a signal processor (e.g. 120), which can send a digital stimulation signal to the source element 710. In some such examples, the DAC of the source element 710 can convert the digital signal to an analog signal and provide the converted signal to the contact electrode 730 or to another element that outputs a current to the contact electrode 730 based on the received analog signal from the DAC. For instance, in some embodiments, such a DAC can be configured to output an analog signal (e.g., an analog voltage) to one or more current source or sink components in order to source or sink current via the contact electrode based on the received digital signal from the controller 700. In general, the digital stimulation signal sent by the signal processor to the source element 710 can comprise an amount of current to be delivered to the contact electrode, and can control an amount of current provided therefrom over time.

The DAC of the source element 710, can convert the digital stimulation signal into an analog signal using a number of bits. In some embodiments, the least significant bits (LSB's) of the digital signal can be considered trim bits which can be used to fine-tune the amount of current delivered to the contact electrode. In various embodiments any number of bits can be used to provide a stimulation signal. For example, in some embodiments, the stimulation signal provided to the DAC of the source element 710 can include at least six bits of precision. In some such embodiments, the DAC can have seven, eight, nine, ten, eleven, or more bits of precision. By using more bits, the source element 710 can have a higher output precision of the digital input signal. For instance, in some examples, using by using 8 bits for the DAC (source element 710), up to 256 distinct levels of current to the contact electrode 730 can be output or otherwise initiated by the DAC via the analog signal provided by the DAC. This can allow for more accurate stimulation by the contact electrode 730.

However, even with generally accurate stimulation, in some examples, the source element 710 can deliver signals and currents to the contact electrode which do not match the desired current. Further, in some embodiments, the source element 710 can source (e.g. deliver) more current to the contact electrode 730 than it sinks (e.g. receives) from the contact electrode. An imbalance in current sourced and sunk by source element 710 to the contact electrode can lead to accumulated electrical charge in the wearer's tissue and/or across the electrode interface, which can cause damage to the wearer (e.g., including damage to the cochlear tissue) and/or damage to the electrode(s) implanted therein. It can thus be desirable to have the same amount of electrical charge sourced to the contact electrode 730 by source element 710 as sunk by source element 710.

While in some embodiments, the source element 710 including the DAC is calibrated/programmed to be as accurate as possible when it is manufactured, over time, it can become less accurate due to various reasons (e.g. drift). For example, source element 710 can include both p-channel metal oxide semiconductor devices (PMOS) and n-channel metal oxide semiconductors (NMOS) devices. PMOS and NMOS devices do not behave the same way over time and may not track each other. The disparity in behavior can result in inaccuracies in the prescribed current from source element 710. In such cases, even when the prescribed amount of current to be sourced/sunk should in theory result in a net-zero charge accumulation, inaccurate current application can lead to the total charge provided to the contact electrode 730 being different than desired and can lead to undesired charge accumulation over time. Accordingly, it can be advantageous to be able to calibrate/program operation of the source element after it has been implanted.

Figure 7B:
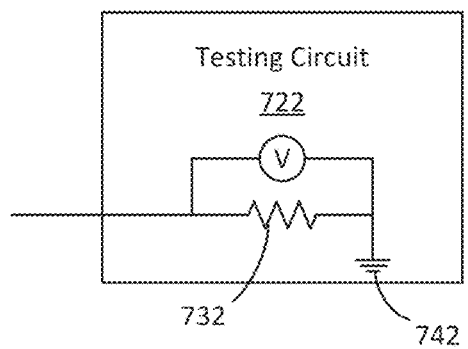
FIG. 7B is an example embodiment of the testing circuit of FIG. 7A.
Figure 7C:
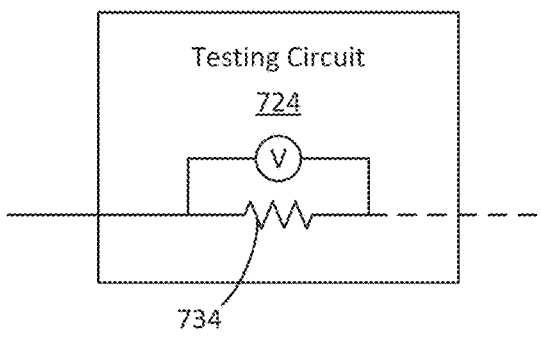
FIG. 7C is an alternative embodiment of the testing circuit of FIG. 7A.

In FIG. 7A, testing circuit 720 can be put into communication with source element 710 by switch 715. In some embodiments, testing circuit can be configured to determine a current being sourced from or sunk to the source element 710. FIGS. 7B and 7C show example implementations of a testing circuit for determining a current provided by the source element. In the embodiment of FIG. 7B, testing circuit 722 includes a precision load 732, for example, a precision resistor or other impedance. The precision load 732 can be any type of impedance, however in some embodiments the precision load 732 comprises a resistor. Further, the precision load 732 can have any value of impedance, but in some embodiments, the value of impedance is a known quantity. In some examples, the precision load 732 is mounted to a circuit board. Testing circuit 722 can also include a way to measure the voltage across the precision load 732 such as a voltmeter. In some embodiments, testing circuit 722 can include an analog to digital converter (ADC) which can convert analog signals (e.g. voltages) to digital representations of the analog signals. In some such examples, such digital signal can be provided to the controller 700 representing the voltage drop across precision load 722. Additionally or alternatively, in some embodiments, testing circuit can include a way to measure the current through the precision impedance such as an ammeter.

In operation, referring to FIG. 7A and FIG. 7B, the switch 715 can direct a current to flow from the source element 710, through the switch 715, and through the precision load to a reference voltage 742. In some examples, the current is a steady-state current which does not change over time. In the example of FIG. 7B, the reference voltage 742 is in electrical communication with the precision load 732. In some examples, reference voltage 742 comprises a system ground. In some embodiments, the testing circuit 722 can measure the voltage across the precision load 732 by measuring the voltage at one side of the precision load 732 opposite the reference voltage 742 relative to the reference voltage 742. In some examples, if the reference voltage 742 comprises a system ground, the testing circuit 722 need not expressly measure the voltage on the system ground 742 side of the precision load 722.

In some examples, the value of the precision load 732 can be known or predetermined. By measuring the voltage and knowing the value of the precision load 732, the current flowing through the precision load 732 can be determined. For example, for a given voltage V and impedance Z, current I can be found by the equation I=V/Z. In some embodiments, the controller 700 determines the current flowing through the precision load 732. In some such embodiments, the controller 700 can receive a digital output corresponding to an analog voltage found across the precision load 732 from an ADC and measure or be programmed with information regarding the impedance of precision load 732. The controller 700 can use such information to determine the current flowing through precision load 732, and therefore the current provided by the source element 710. The calculated current can also be referred to as the measured current or determined current. In some embodiments, the calculated current, delivered through the precision load 732, can be compared to a desired current.

FIG. 7C is an alternative testing circuit 724 which can measure the current flowing through a precision load. The testing circuit is in communication with contact electrode 730 as shown by the dashed lines of FIG. 7A and FIG. 7C. In operation, referring to the embodiment of FIG. 7A and FIG. 7C, the switch can direct a current to flow from the source element 710, through the switch 715, through the precision load 734 of the testing circuit 724, and through contact electrode 730. In this operation, the current flowing through the precision load 734 can be calculated by measuring the potential difference (e.g. voltage) across the precision load 734. In some such configurations, no system ground is present for measuring the potential difference across the precision load 734. In some embodiments, the testing circuit 724 of FIG. 7C can be used to determine the current provided by the source element 710 while using the current from source element 710 to stimulate cochlear tissue.

As described, in some embodiments, testing circuit is also connected to a controller 700. In the illustrated embodiment of FIG. 7A, the controller can interface with testing circuit 720 such that it can be configured to determine the amount of electrical current flowing through a precision load in the testing circuit 720. In some embodiments, the controller 700 is separate from the testing circuit 720, however, in some examples, at least a portion of the controller is integrated with the testing circuit such that the testing circuit 720 effectively determines the amount of electrical current flowing through a precision load.

In the illustrated embodiment of FIG. 7A, the controller 700 can be in communication with the source element 710 in addition to being in communication with the testing circuit 720. In such a configuration, the controller 700 can control various aspects of the source element 710. For example, the controller 700 can cause a stimulator (e.g. 130 of FIG. 1) to emit an electrical current from the source element 710. In such an example, the controller 700 can provide a signal to source element 710 such that source element 710 activates and emits an electrical current. The controller 700 can provide a signal to cause source element 710 to output a prescribed electrical current.

Current can be directed to testing circuit 720 via switch 715, and the testing circuit (e.g., the testing circuit 722 of FIG. 7B or 724 of FIG. 7C) can be used to measure the current emitted from the source element 710. In some embodiments, the controller compares the measured current to the prescribed current (current that source element 710 is supposed to deliver). For example, source element 710 can be configured to deliver a current of 1 milliamp (e.g. the prescribed current) to the testing circuit 720 including a precision load. However, due to various issues and/or inaccuracies as previously discussed, the measured current flowing through the precision load can be less than or greater than the prescribed 1 milliamp. In the case that the desired current and the measured current differ, the source element 710 can be adjusted (e.g. calibrated/programmed) such that the current measured at the testing circuit 722 matches the prescribed current from the controller 700. In some examples, such calibration can include changing the output current produced by the DAC of the source element 710. This can include changing the LSB's of the DAC to reflect an increase or decrease in the amount of current desired. Additionally or alternatively, calibration can be performed in the controller 700 (e.g., the signal processor), wherein the signal provided from the controller 700 to the source element 710 for a given prescribed current is modified. For example, the controller 700 can be configured to adjust the LSB's of a signal provided to the DAC for a prescribed current so that the current output from the source element changes for a given prescribed current. In some such examples, the controller 700 can be configured to adjust the signal provided to the DAC by an offset value, for example, based on the difference between the prescribed current and the measured current. In some such examples, offset values can be associated with differences between the prescribed current and the measured current based on values stored in a lookup table or based on an equation.

In some embodiments, the source element can include multiple DACs. In some such examples, the source element comprises a signal generation DAC configured to generally operate as described herein, and a calibration DAC in parallel with the signal generation DAC. In some embodiments, controller 700 can be configured to operate the signal generation DAC to provide a prescribed current and calibrate the applied current by adjusting operation of the calibration DAC (e.g., adjusting a digital input thereto in order to adjust the output thereof). Adjusting operation of the calibration DAC can fine-tune the overall output of the source element in order to source or sink a calibrated current from the corresponding contact electrode.

Figure 7D:
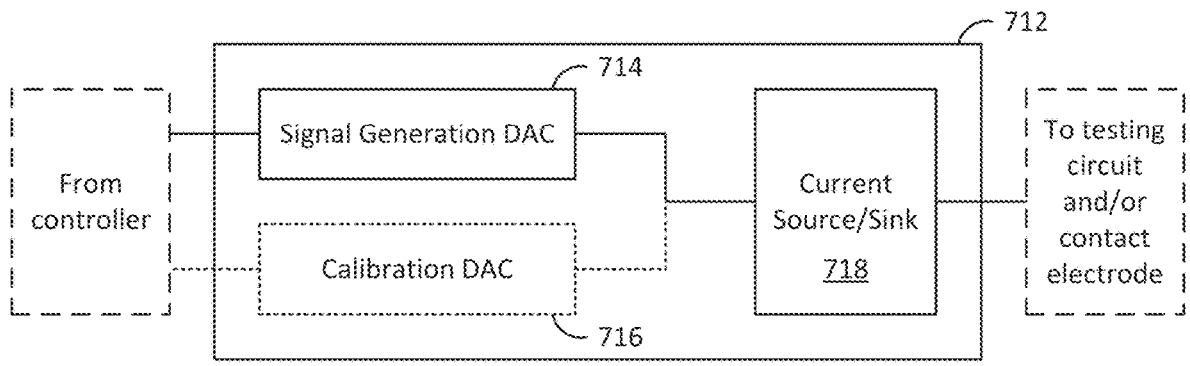
FIG. 7D shows an example source element including a signal generation DAC and a calibration DAC.

FIG. 7D shows an example source element including a signal generation DAC and a calibration DAC. As shown, source element 712 includes signal generation DAC 714 configured to receive a signal (e.g., a digital signal) from a controller (e.g., controller 700) and output a signal to a current source/sink 718 that can be configured to source or sink a current toward a testing circuit (e.g., 720) and/or contact electrode (e.g., 730) such as described herein based on the signal received from the signal generation DAC 714. In some embodiments, source element 712 further includes a calibration DAC 716 configured to receive a signal from the controller and output a signal to the current source/sink 718. In some examples, the signal from the calibration DAC 716 can be used to adjust the amount of current source/sunk via the source element 712 for calibration. Additionally, while shown as combining with the signal from signal generation DAC 714, the signal from the calibration DAC 716 can be provided to the current source/sink 718 separately from the signal from the signal generation DAC 714.

In general, adjusting the output of the source element, such as done in response to a detected discrepancy between a prescribed current and a measured current, can be done via adjusting operation of the controller 700 (e.g., within the signal processor), operation of the source element 710 (e.g., operation of a DAC), or a combination thereof In some embodiments, the amount of current provided by the source element 710 can be adjusted based on the current measured at the testing circuit 720 such that the current measured at testing circuit 720 matches the prescribed current. By adjusting the amount of current output by the source element 710 such that the measured current matches the prescribed current, the accuracy of the signal output by source element 710 can be increased. In some embodiments, a controller 700 adjusts the output current of the source element 710 based on the determined (e.g. calculated) amount of electrical current which flows through the precision load.

Adjusting (e.g. calibrating) the output current of the source element 710 can be repeated any number of times. For example, in some embodiments, after adjusting the output of the source element 710 based on a measured current, the same source element can be tested again using the same prescribed current to confirm that the updated operation is accurate, or to further refine the operation of the source element 710. Additionally or alternatively, in some examples, the adjustment of the output current of the source element 710 is done using a variety of prescribed current values.

In some examples, the controller can instruct the source element 710 to output a first prescribed current. The controller 700 can then compare the first prescribed current with the corresponding measured current flowing through the precision impedance of the testing circuit 720. The controller can also instruct the source element 710 to output a second prescribed current. The controller 700 can then compare the second prescribed current with the corresponding measured current flowing through the precision impedance of the testing circuit 720. From these two comparisons, a line of best fit (e.g. calibration curve) can be used to adjust the output current of the source element accordingly. In some examples, more than two prescribed current values can be used to create the line of best fit for a source element. In some embodiments, a range of output currents which encompasses the entire range of the DAC of the source element can be used to create the line of best fit. By using a line of best fit for calibrating the output current of the source element, the accuracy of the current output from the source element relative to the prescribed current across a range of values can be increased.

After the adjustment of the output current of source element 710 using testing circuit 720 has been completed, the switch 715 can be switched to connect source element 710 to contact electrode 730. Thus, the calibrated source element 710 can be used with the contact electrode 730 to accurately provide prescribed current to the cochlear tissue. In some embodiments, by calibrating source element 710, the charge delivered to the cochlear tissue by contact electrode can remain neutral can be accurately controlled to maintain charge neutrality over time.

In some embodiments, adjustment of the source element 710 is done in vivo. Additionally, in some embodiments, adjustment of the source element 710 is done after the source element 710 has been calibrated in a factory or other space outside of a patient's body. Alternatively, in some embodiments, adjustment of the source element 710 is done in lieu of any calibration outside of a patient's body. Being able to adjust the source element 710 in vivo has many benefits over exterior calibration including that the adjustment can be performed at any time without removal of the source element from the patient and that charges can be more easily balanced, possibly leading to less damage of the cochlear nerve.

In an example operation of the embodiment of FIG. 7A, the source element 710 is initially connected to contact electrode 730 through switch 715. After a period of time (or before the first use), it may be desired to calibrate the amount of output current generated by the source element 710 and delivered to the contact electrode 730 to ensure the prescribed amount of current is provided during stimulation. At such a time, the controller 700 directs the switch 715 such that the connection between the source element 710 and the contact electrode 730 is severed and a connection between the source element 710 and the testing circuit 720 is made. The controller 700 then causes the source element 710 to deliver a prescribed current through the testing circuit 720. The current from the source element 710 can be directed to a precision load (e.g., 732) within the testing circuit 720. The controller 700 determines the amount of electrical current flowing through the precision load by measuring a voltage across the known impedance of the precision load (e.g., by measuring a voltage on one side of the precision load relative to a system ground). The controller 700 compares the prescribed current with the determined current (e.g. measured current) and adjusts the operation of the source element 710 so that the measured current matches the prescribed current. After at least one adjustment, the controller 700 switches the switch 715 to connect the source element 710 with the contact electrode 730. The example operation of the embodiment of FIG. 7A can be repeated any number of times.

Figure 8:
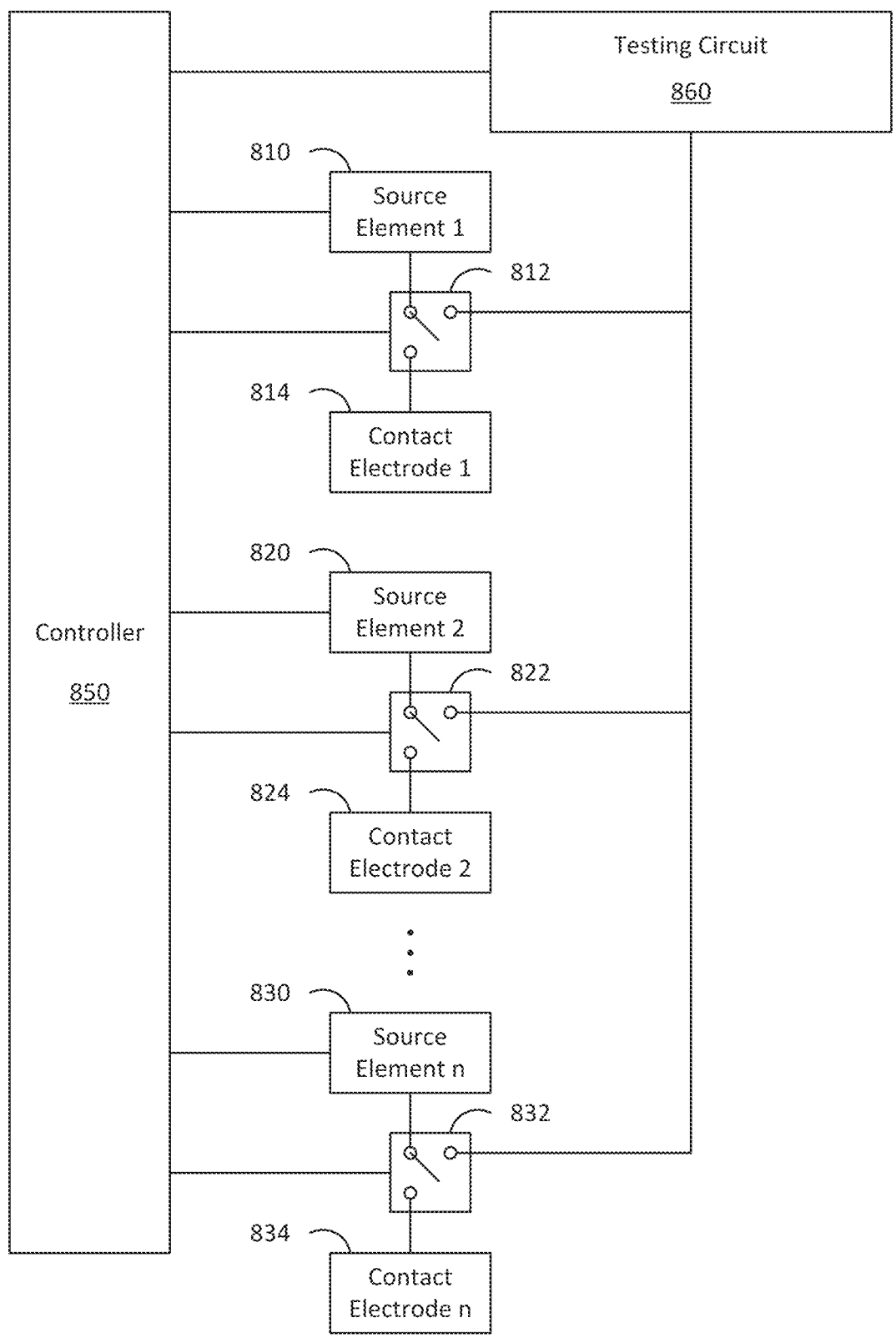
FIG. 8 is a high-level electrical schematic showing communications between various components of a cochlear implant system for multiple contact electrodes including a testing circuit.

Moving to FIG. 8, FIG. 8 is a high-level electrical schematic showing communications between multiple source elements, multiple switches, multiple contact electrodes, a controller, and a testing circuit. As in the embodiment of FIG. 7A, each switch of FIG. 8, which can be a part of switching network, can selectively connect a source element with either a testing circuit or a corresponding contact electrode. For example, in FIG. 8, a first source element 810 can be in communication with a first contact electrode 814 or a testing circuit 860 through first switch 812. Further, a second source element 820 can be in communication with a second contact electrode 824 or the testing circuit 860 through a second switch 822. A controller 850 can control or otherwise manipulate each of the switches to selectively connect each source element with each corresponding contact electrode or the testing circuit 860. In various embodiments, controller 850 can be embodied via one or more components such as those described with respect to controller 700 in FIG. 7.

In various embodiments, this configuration of elements can be repeated (e.g. consecutively) such that an n number of source elements 830 are selectively connected to an n number of contact electrodes 834 or a testing circuit 860 through an n number of switches 832 as illustrated in FIG. 8. In some embodiments, the n number of contact electrodes is at least eight. In such embodiments, at least eight source elements and at least eight switches are used with the at least eight contact electrodes. In some embodiments, ten, twelve, or more contact electrodes are used with a corresponding amount of source elements and switches. In some examples, the switching network can include elements other than the switches while in alternative examples, the switching network is comprised entirely of switches.

Continuing with the example of FIG. 8, the testing circuit 860 can include a precision load, such as shown in the example testing circuits of FIGS. 7B and 7C. In some examples, testing circuit 860 can include a way to measure the voltage across the precision load or otherwise communicate the voltage to the controller 850. In some cases, controller 850 can measure a voltage across the precision load directly. While the example of FIG. 8 only includes a single testing circuit 860, multiple testing circuits can be used. Further, in some examples, more than one precision load can be used including a more than one prevision impedances within a single testing circuit. However, the embodiment of FIG. 8 can be advantageous over other configurations including multiple testing circuits and/or multiple precision loads as it can require fewer resources and take up less physical space.

Further, in the embodiment of FIG. 8, a controller 850 is in communication with the plurality of source elements in addition to the plurality of switches. In the illustrated example of FIG. 8, the controller 850 can control each of the source elements and cause them to emit an electrical current. The controller 850 can be in communication with testing circuit 860. In such a configuration, the controller 850 can control and/or determine different aspects of the testing circuit 860. For example, the controller 850 can determine the amount of electrical current flowing through a precision load present in the testing circuit 860. In some embodiments, the controller 850 can use the determined amount of current flowing through the testing circuit 860 to adjust a source element such as described herein.

In some embodiments, multiple controllers can be used and, in some embodiments, a controller can be a part/portion of other elements of the cochlear implant system. For example, the controller can be a part/portion of the signal processor (e.g. 120 of FIG. 1) and in some embodiments, the controller is the signal processor. Further, in some examples, the switching network, which includes switches, can also be included as part of the signal processor. Moreover, in some example, the testing circuit can be included as part of the signal processor. In some embodiments, the signal processor includes a switching network and a testing circuit and in some further embodiments, the signal processor includes a controller in addition to the signal processor and the switching network. In various embodiments, any combination of the switching network, the testing circuit, and the controller can be integrated with the signal processor.

As disclosed with respect to the operation of FIG. 7A, an output current of a source element can be measured and adjusted (e.g. calibrated) through the use of a testing circuit and a controller. The operation of FIG. 7A is disclosed relative to a single source element which can be connected to a single contact electrode. However, the operation of FIG. 7A can be repeated for multiple source elements connected to multiple contact electrodes.

In an example operation of the embodiment of FIG. 8, a first source element 810 can initially be connected to a first contact electrode 814 through a first switch 812. The first source element 810 can deliver an output current to the first contact electrode 814. The controller 850 can be configured to direct the first switch 812 to sever connection between the first source element 810 and the first contact electrode 814 and establish a connection between the first source element 810 and the testing circuit 860. The controller 860 can cause the first source element 810 to deliver a prescribed output current through the testing circuit 860, which in some examples flows through a precision load within the testing circuit 860. The controller can determine the amount of electrical current flowing through the precision load, for example, by measuring a voltage across the known impedance of the precision load. The controller 860 can compare the prescribed current from the first source element 810 with the determined current, and adjust the output current of the first source element 810 such that the determined current matches the prescribed current. This process can be repeated any number of times for the first source element 810. Once the first source element 810 has been adjusted (e.g. calibrated), the controller can adjust a second source element 820 connected to a second electrode 824 or the testing circuit 860 in a similar manner as the first source element 820 is adjusted as described above. Adjusting the second source element 820 can be done any number of times. Further, the process of adjusting a source element can be repeated n times for each of n number of source elements, for example, until all source elements have been adjusted. In such a process, each individual source element can be adjusted one after another (e.g. consecutively) until all the source elements are adjusted. In some embodiments, eight or more source elements are adjusted to output current for eight or more contact electrodes. In some embodiments, ten or twelve source elements can be adjusted.

In an alternative operation of the embodiment of FIG. 8, the controller 850 causes a source element to emit a prescribed electrical current to the testing circuit 860 and through a precision load. The controller determines the current flowing through the precision load. However, instead of comparing and adjusting the output current of the source element relative to a known current, the controller 850 causes another source element to emit a prescribed electrical current to the testing circuit 860 and through the precision load. The controller determines the current flowing through the precision load for the second source element. This process can be repeated until the controller 850 has determined the respective current flowing through the precision load for all the source elements given the prescribed current. In some examples, the respective prescribed current for each of the source elements is the same during such a process.

Once the controller 850 has the determined currents for each of the source elements, it can determine characteristics of the determined currents. For example, the controller 850 can determine a first current flowing through testing circuit 860 from a first source element and determine a second current flowing through testing circuit 860 from a second source element. The controller 850 can then determine various characteristics, such as the minimum amount of electrical current, the maximum amount of electrical current, and the average amount of electrical current. Further, this process can be expanded to include n number of determined currents flowing through testing circuit 860 from an n number of source elements.

The controller 850 can use the determined characteristics (e.g. average amount of current) and compare them to the prescribed current. For example, an average current of 1.5 milliamps applied to testing circuit 860 can be compared to a prescribed current of 1.0 milliamps, a difference of 0.5 milliamps. If the average current is not equal to the prescribed current, the controller can adjust each source element such that the average current of all the source elements is the same as the prescribed current. In some embodiments, the controller 850 adjusts all the source elements the same amount to shift the average amount of current toward the prescribed current. In some embodiments, adjusting the output of each source element includes adjusting the LSB of each DAC of the source elements by the same amount.

Adjusting all the source elements in example operation of FIG. 8 can be advantageous as the adjustment is only done in one step instead of on a per-source element basis. However, in some examples, adjusting all the source elements in the same step can be a first step before the controller 850 adjusts each individual source element. For example, all the source elements can be adjusted the same amount such that their average output current is equal to a desired (e.g. prescribed) current. Each individual source element can be subsequently adjusted such that each individual output current is equal to a prescribed current. In such an example, the initial adjusting of all the source elements can put their respective output currents closer to the prescribed current, with the secondary, individual adjusting of each source element putting the output currents at the prescribed current. Thus, in some examples, a bulk calibration of the output currents of the source elements can be performed before a fine calibration.

Adjustment of the source elements can be done at any time, however, in some embodiments, adjustment is done at specific times. For example, it can be advantageous to adjust the source elements soon after the cochlear implant system is implanted into a wearer to ensure accurate stimulation and avoid charge accumulation as soon as possible, limiting any possible damage to the cochlear tissue or implanted components. Additionally or alternatively, calibration can be done after an audiologist determines specific settings (e.g. setting a transfer function) of the cochlear implant system after it is implanted. Further, in some embodiments, adjustment can be done periodically, such as at auto-programmed times, or at discrete times, such as when a user initiates an adjustment (e.g., via a charger or other external component in communication with the implanted system). Other periods of time for when adjustment is performed are contemplated, such as when prescribed by an audiologist, and a person of ordinary skill will understand that the present disclosure is not limited to the examples provided.

Figure 9:
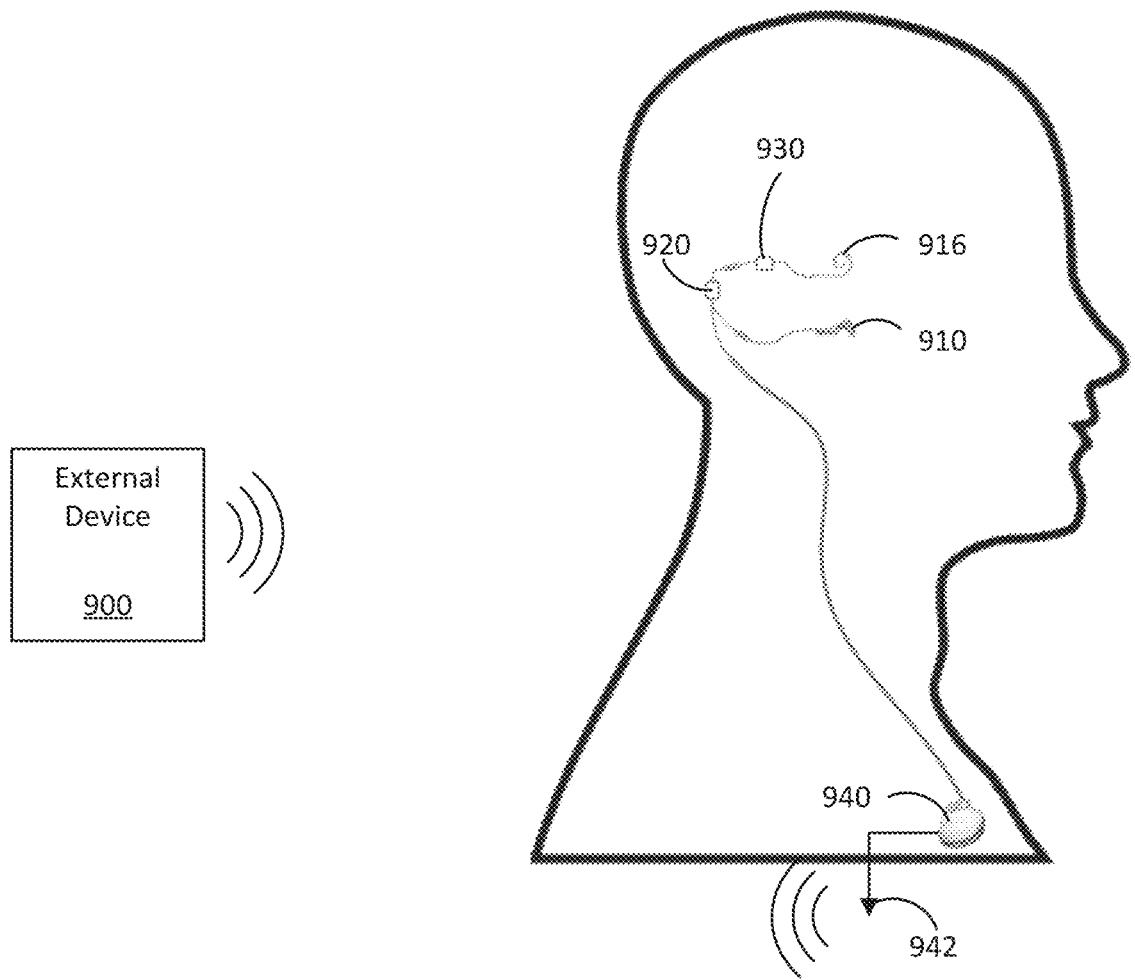
FIG. 9 shows a schematic illustration of an example fully implantable cochlear implant system with an external device for programming.

Moving to FIG. 9, FIG. 9 shows a schematic illustration of an example fully implantable cochlear implant system with an external device for programming. The illustrated embodiment of FIG. 9 includes a cochlear electrode 916 in communication with a stimulator 930 and further in communication with a signal processor 920. The signal processor 920 is also in communication with a middle ear sensor 910 and an implantable battery and/or communication module 940. In some examples, the signal processor includes a controller. Additionally, implantable battery and/or communication module 940 can include or otherwise be in communication with an antenna 942 which is in wireless communication with an external device 900. The antenna 942 can be located in the interior of the wearer, the exterior of the wearer, or a combination thereof. The antenna 942 can pick up wireless signals from the external device 900 and transmit the wireless signals into the implantable battery and/or communication module 940. In some examples, the wireless signals can include a wireless command. In some such examples, the wireless command can be sent from the external device 900 and reach controller (e.g. in signal processor 920).

In operation of the illustrated embodiment, the external device 900 can initiate and/or perform an adjustment operation such as those described elsewhere herein. For example, the external device 900 can initiate a controller to calibrate one or more source elements such as described elsewhere herein in response to a wireless command. For instance, in some embodiments, external device can initiate an adjustment process through implantable battery and/or communication module 940 with a different device instructing and/or performing the adjustment process. Additionally or alternatively, in some examples, the external device 900 can perform one or calibration steps. For instance, in some examples, external device 900 can designate a prescribed current to be provided from a source element and receive information indicative of the resulting current received at a testing circuit. The external device 900 can be configured to adjust the output of the source element based on the prescribed current and the received information indicative of the resulting current. For example, in some embodiments, external device 900 can communicate to implantable battery and/or communication module 940 various commands and/or values in order to adjust the stimulator 930 to output a current which is the same as the prescribed current. In other embodiments Additionally or alternatively, in some embodiments, adjustments can be done manually. For example, an audiologist can connect to a portion of the cochlear implant system (e.g. programmer 100 of FIG. 1) and manually control aspects of the adjustment process (e.g. current levels). In some embodiments, manual adjustments can be done remotely using an external device 900. In some examples, adjustment is done for one or more electrodes and in some examples, adjustment is done for one or more magnitudes of prescribed current.

Figure 10:
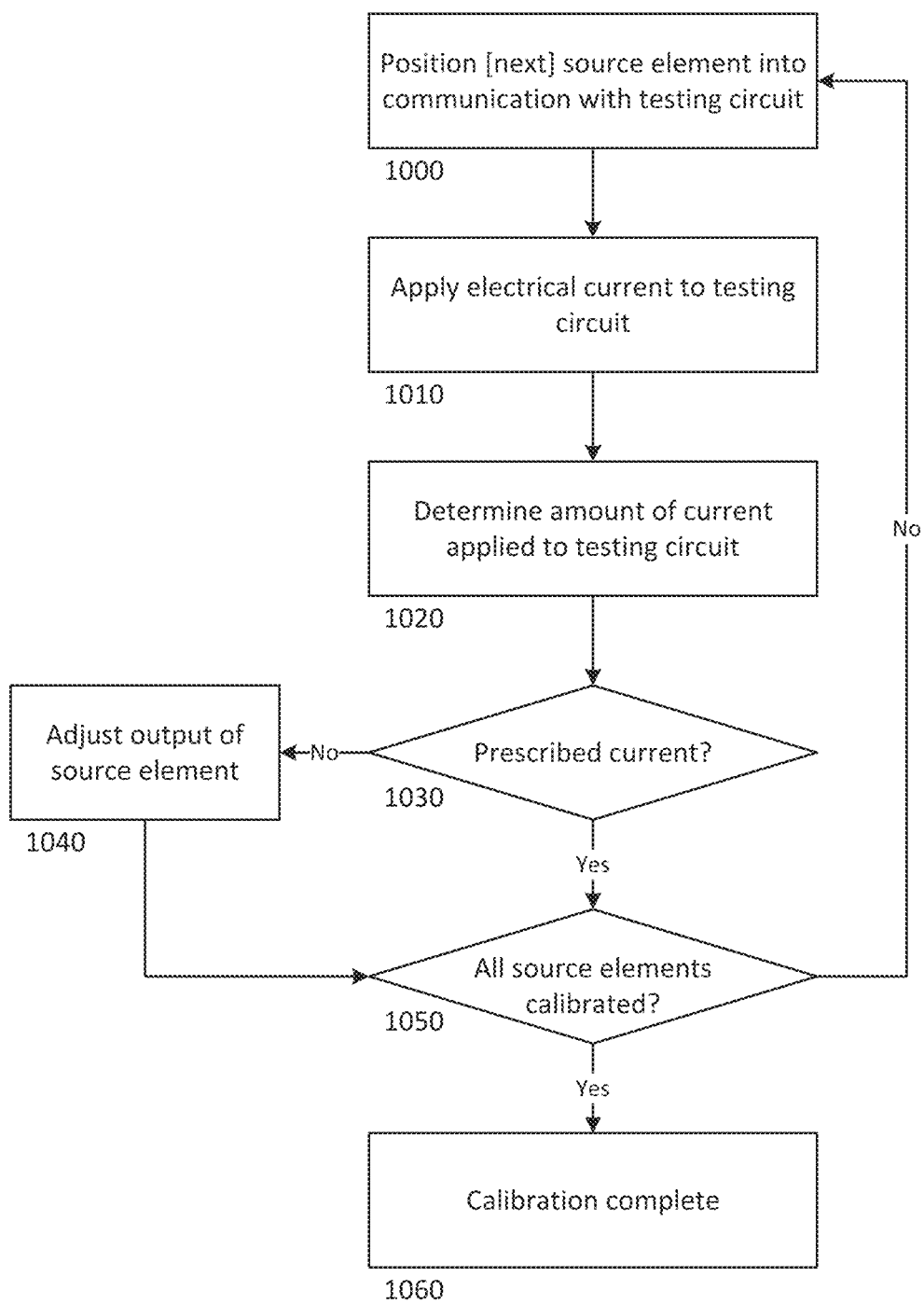
FIG. 10 is an example adjustment process using a controller for a cochlear implant system.

FIG. 10 is an example adjustment (e.g. calibration) process using a controller for a cochlear implant system. Beginning with step 1000, the controller positions a source element into communication with a testing circuit. In some embodiments, this step includes switching a switch from a position in which the source element is in communication with a contact electrode to a different position in which the source element is in communication with a testing circuit. Moving to step 1010, the controller applies electrical current to the testing circuit. In some embodiments, this step includes causing a stimulator to emit an electrical current from the source element to the testing circuit. Moving to step 1020, the controller determines the amount of current applied to the testing circuit. In some embodiments, this step can include measuring a voltage across a precision load, for example, having a known impedance, within the testing circuit and calculating the amount of current applied to the testing circuit. As described herein, in some examples, this includes measuring a single voltage relative to a system ground. Moving to step 1030, the controller determines if the amount of current applied to the testing circuit is the same as the prescribed current. In some embodiments, the controller further determines the difference between the current applied to the testing circuit and the prescribed current. If the comparison of step 1030 results in a logical no (e.g. the amount of current applied to testing circuit does not equal the prescribed current) the controller can adjust the output of the source element as in step 1040. In some embodiments, the controller adjusts the output current of the source element such that it is the same as the prescribed current.

In the illustrated example, if the amount of current applied to testing circuit does equal the prescribed current, or if the output of the source element has been adjusted as in step 1040, the process moves to step 1050. In step 1050, the controller can determine if all the source elements have been calibrated. If all the source elements have not been calibrated, the process starts over with step 1000, comprising positioning a next source element into communication with the testing circuit. However, if all the source elements have been calibrated, the process can be finished with step 1060 wherein the calibration is complete.

It will be appreciated that, while in some embodiments, the process of FIG. 10 can be carried out via a controller, the controller need not perform each step shown in FIG. 10. For instance, in some such embodiments, the controller need not literally determine a binary or logical "yes or no" answer in steps 1030 and 1050. For instance, in some examples, the controller can be configured to adjust an output of a source element based on a difference between a measured and prescribed current. In some such examples, if the measured current is equal to the prescribed current, an adjustment step can include an "adjustment" equal to zero rather than determining a binary "yes" that the prescribed and measured current are equal and skipping the adjustment step.

Figure 11:
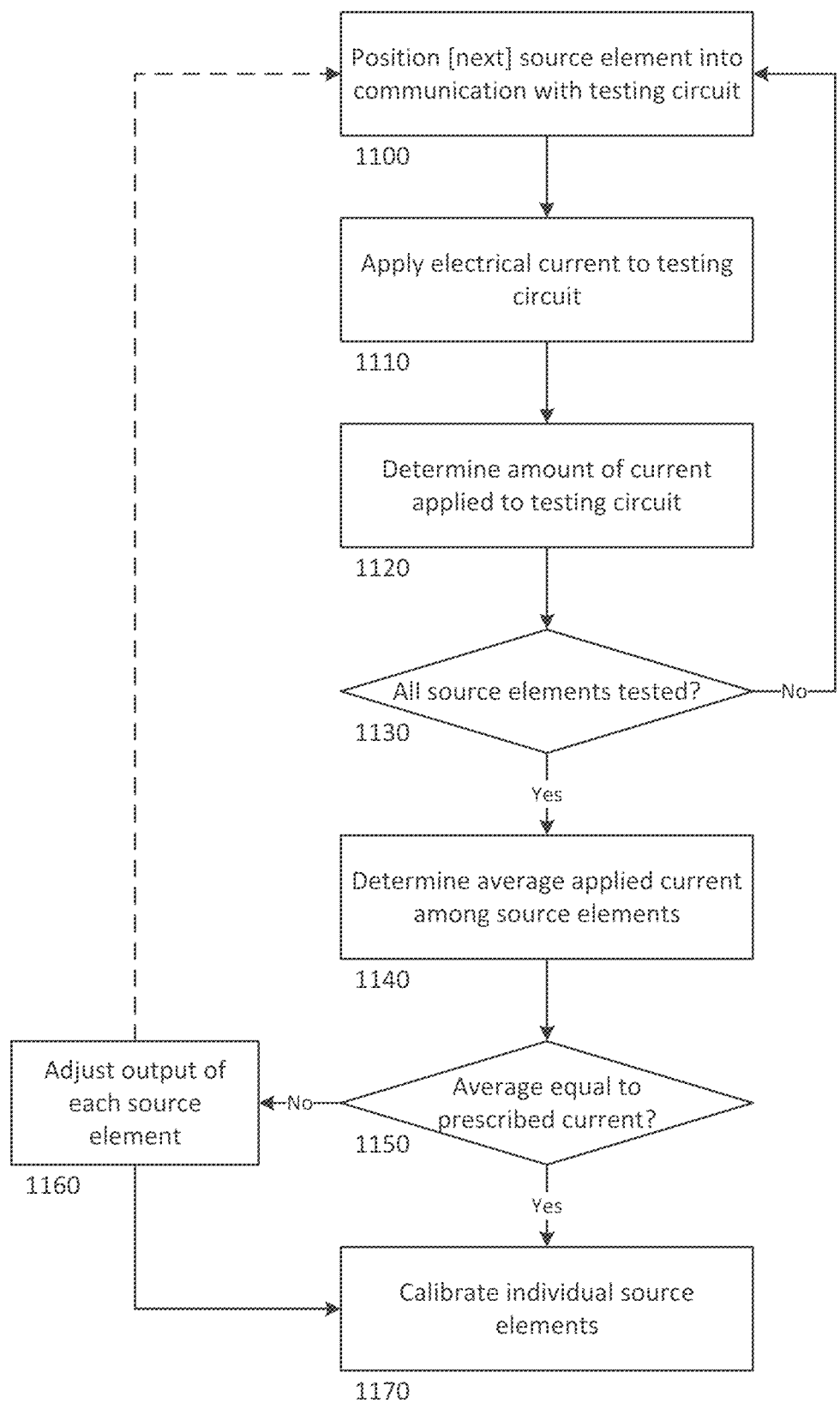
FIG. 11 is an alternative example adjustment process using a controller for a cochlear implant system.

Moving to FIG. 11, FIG. 11 is an alternative example adjustment (e.g. calibration) process (e.g. method) using a controller for the cochlear implant system. Beginning with step 1100, the controller positions a source element into communication with a testing circuit. In some embodiments, this step includes switching a switch from a position in which the source element is in communication with a contact electrode to a different position in which the source element is in communication with a testing circuit. Moving to step 1110, the controller applies electrical current to the testing circuit. In some embodiments, this step includes causing a stimulator to emit an electrical current from the source element to the testing circuit. Moving to step 1120, the controller determines the amount of current applied to the testing circuit. Similar to described elsewhere herein, in some embodiments, this step can include measuring a voltage across a precision load having a known impedance within the testing circuit and calculating the amount of current applied to the testing circuit.

Moving to step 1130, the controller can determine if all the source elements have been tested. If all the source elements have not been tested, the process starts over with step 1100, positioning a next source element into communication with the testing circuit. However, if all the source elements have been tested, the adjustment process can continue with step 1140. In step 1140, the controller can determine an average applied current among the source elements. In some embodiments, this step includes determining an average current flowing through a precision load of the testing circuit among all the source elements. Moving to step 1150, the controller can compare the average applied current among the sources to a prescribed current. In the case that the average applied current is not the same as the prescribed current, the controller can perform step 1160, in which the controller adjusts the output of each source element, for example, so that the average current equals the prescribed current.

In some embodiments, after the controller adjusts the output of each source element, or if the average current was equal to the prescribed current, the controller can perform step 1170, wherein the controller adjusts (e.g. calibrates) the individual source elements. In some embodiments, this subsequent adjustment (e.g. calibration) is done in accordance with the process outlined in FIG. 10. Such individual source calibration can be used to fine tune each source element after bulk calibrating the source elements by adjusting their outputs based on the average measured current.

In some examples, after the controller adjusts the output of each source element in step 1160, the process can start over with step 1100 wherein the controller positions the next source element into communication with the testing circuit. For example, the process can include testing each source element, averaging the resulting currents, and adjusting each source element to shift the average applied current toward the prescribed current multiple times, for example, prior to calibrating the individual source elements in step 1170.

Similar to described with respect to FIG. 10, in some examples, the process of FIG. 11 can be performed by a system controller. However, in some such examples, the controller need not determine a binary/logical "yes" or "no" at steps 1130 or 1150.

Various non-limiting embodiments have been described. These and others are within the scope of the following claims.

The invention claimed is:

1. A cochlear implant system comprising:
 a cochlear electrode comprising a plurality of contact electrodes;
 a stimulator in electrical communication with the cochlear electrode, the stimulator including a plurality of source elements, each of the plurality of source elements being in electrical communication with a corresponding one of the plurality of contact electrodes of the cochlear electrode;
 an input source configured to receive a stimulus signal and generate an input signal based on the received stimulus signal;
 a signal processor in communication with the stimulator and the input source, the signal processor being programmed with a transfer function and being configured to receive the input signal from the input source and output a stimulation signal to the stimulator based on the received input signal and the transfer function;
 a testing circuit;
 a switching network configured to selectively place each of the plurality of source elements into electrical communication with the testing circuit; and
 a controller in communication with the stimulator, the testing circuit, and the switching network and configured to:
 control the switching network to place one of the plurality of source elements into communication with the testing circuit; and
 (a) cause the stimulator to emit an electrical current from the one of the plurality of source elements in communication with the testing circuit;
 (b) determine an amount of electrical current emitted from the one of the plurality of source elements via the testing circuit; and
 (c) adjust the output of the one of the plurality of source elements based on the determined amount of electrical current.

2. The cochlear implant system of claim 1, wherein the adjusting the output of the one of the plurality of source elements based on the determined amount of electrical current comprises comparing the determined amount of electrical current to a desired amount of electrical current and adjusting the output of the source element based on the comparison.

3. The cochlear implant system of claim 1, wherein the testing circuit comprises a precision load such that, when the stimulator emits the electrical current from the one of the plurality of source elements in communication with the testing circuit the electrical current flows through the precision load.

4. The cochlear implant system of claim 3, wherein the determining the amount of electrical current emitted from the one of the plurality of source elements comprises measuring a voltage across the precision load.

5. The cochlear implant system of claim 4, wherein the testing circuit comprises an analog to digital converter (ADC), and wherein the measuring the voltage across the precision load comprises receiving an output from the ADC corresponding to the voltage across the precision load.

6. The cochlear implant system of claim 5, wherein the testing circuit further comprises a reference voltage in electrical communication with the precision load such that the electrical current from the stimulator flows through the precision load and then to the reference voltage.

7. The cochlear implant system of claim 6, wherein the measuring the voltage across the precision load comprises measuring the voltage at one side of the precision load opposite the reference voltage.

8. The cochlear implant system of claim 1, wherein the controller is configured to:
control the switching network to consecutively place each of the plurality of source elements into communication with the testing circuit; and
perform steps (a), (b), and (c) for each of the plurality of source elements.

9. The cochlear implant system of claim 1, wherein each of the plurality of source elements comprises a corresponding digital to analog converter (DAC) configured to receive a digital input signal and output an analog signal in response to the digital input signal causing a current to be emitted from the corresponding source element.

10. The cochlear implant system of claim 9, wherein each DAC is configured to output a current in response to the received digital input signal.

11. The cochlear implant system of claim 9, wherein each DAC is configured to output a voltage in response to the received digital input signal, and wherein the voltage causes a corresponding current to be output from the corresponding current source.

12. The cochlear implant system of claim 9, wherein:
each of the plurality of source elements comprises a signal generation DAC and a calibration DAC arranged in parallel with the signal generation DAC;
the causing the stimulator to emit the electrical current comprises emitting the electrical current via the signal generation DAC; and
the adjusting the output of the one of the plurality of source elements based on the determined amount of electrical current comprises adjusting operation of the calibration DAC.

13. The cochlear implant system of claim 9, wherein the DAC of each of the plurality of source elements comprises at least six bits of precision.

14. The cochlear implant system of claim 9, wherein the controller is configured to:
control the switching network to consecutively place each of the plurality of source elements into communication with the testing circuit;
for each of the plurality of source elements:
provide a first digital signal to the corresponding DAC, the first digital signal corresponding to a first predetermined current level; and
determine the resulting current flowing from the source element;
determine an average amount of current flowing from each of the plurality of source elements;
compare the determined average amount of current to the first predetermined current level; and
adjust each of the DACs by the same amount to shift the average amount of current toward the first predetermined current level.

15. The cochlear implant system of claim 1, wherein:
the controller is configured to perform steps (a) and (b) for each of a plurality of electrical current values; and wherein
step (c) comprises determining a best fit adjustment across the plurality of electrical current values and adjusting the output of the source element according to the determined best fit adjustment.

16. The cochlear implant system of claim 1, wherein each of the plurality of source elements is capable of sourcing and sinking current.

17. The cochlear implant system of claim 1, wherein the cochlear electrode comprises at least eight contact electrodes.

18. The cochlear implant system of claim 1, further comprising an implantable battery and/or communication module in communication with the signal processor and being configured to provide electrical power to the signal processor; and wherein the controller is the signal processor.

19. The cochlear implant system of claim 1, further comprising an external component, and wherein the controller is configured to perform steps (a)-(c) in response to a wireless command received from the external component.

20. The cochlear implant system of claim 1, wherein the input source comprises a middle ear sensor.

21. The cochlear implant system of claim 1, wherein the switching network and the testing circuit is included in the signal processor.

22. A method of calibrating current flow in a cochlear implant system comprising:
manipulating a switching network to position a first source element corresponding to one of a plurality of contact electrodes of a cochlear electrode into electrical communication with a testing circuit;
providing an electrical current from the first source element to the testing circuit;
determining an amount of electrical current provided by the first source element via the testing circuit; and
adjusting an output of the first source element based on the determined amount of electrical current.

23. The method of claim 22, further comprising:
applying a first current signal to the first source element, the first current signal corresponding to a first predetermined amount of current; and wherein
the applying the electrical current from the first source element to the testing circuit is in response to the applied first current signal; and
the adjusting the output of the first source element based on the determined amount of electrical current comprises comparing the determined amount of electrical current to the first predetermined amount of current and adjusting the output of the first source element based on the comparison.

24. The method of claim 23, wherein the adjusting the output of the first source element comprises adjusting the first current signal applied to the first source element.

25. The method of claim 22, further comprising:
manipulating the switching network to position each of a plurality of source elements, each corresponding to one of the plurality of contact electrodes, into electrical communication with the testing circuit; and, for each of the plurality of source elements:
applying the electrical current from the source element to the testing circuit;
determining the amount of electrical current applied from the source elements via the testing circuit; and
adjusting the output of the source element based on the determined amount of electrical current.

26. The method of claim 25, wherein:
for each of the plurality of source elements, the applying the electrical current from the source element to the testing circuit comprises applying a first current signal to the source element, the first current signal corresponding to a first predetermined current level.

27. The method of claim 26, further comprising:
determining an average amount of electrical current applied from each of the plurality of source elements; and
comparing the average amount of electrical current among the electrical current to the first predetermined current level; and wherein
the adjusting the output of each of the plurality of source elements comprises adjusting the output of each of the plurality of source elements by the same amount based on the comparison of the average amount of electrical current among the electrical current to the first predetermined current level.

28. The method of claim 27, wherein each of the plurality of source elements comprises a digital to analog converter (DAC), and wherein adjusting the output of each of the plurality of source elements by the same amount comprises adjusting an input to each of the plurality of DACs by the same amount.

* * * * *